(12) United States Patent
Yang

(10) Patent No.: US 10,407,465 B2
(45) Date of Patent: Sep. 10, 2019

(54) PEPTIDES ENHANCING NEURONAL OUTGROWTH AND APPLICATION THEREOF

(71) Applicant: Schweitzer Biotech Company Ltd., Taipei (TW)

(72) Inventor: Ying-Chen Yang, Taipei (TW)

(73) Assignee: SCHWEITZER BIOTECH COMPANY LTD., Taipei (TW)

( * ) Notice: Subject to any disclaimer, the term of this patent is extended or adjusted under 35 U.S.C. 154(b) by 0 days.

(21) Appl. No.: 15/520,605

(22) PCT Filed: Oct. 20, 2015

(86) PCT No.: PCT/CN2015/092336
§ 371 (c)(1),
(2) Date: Apr. 20, 2017

(87) PCT Pub. No.: WO2016/062242
PCT Pub. Date: Apr. 28, 2016

(65) Prior Publication Data
US 2017/0362274 A1    Dec. 21, 2017

Related U.S. Application Data

(60) Provisional application No. 62/065,960, filed on Oct. 20, 2014.

(51) Int. Cl.
| | |
|---|---|
| *C07K 7/06* | (2006.01) |
| *A61K 38/08* | (2019.01) |
| *A61P 25/00* | (2006.01) |
| *A61K 38/00* | (2006.01) |
| *A61K 38/16* | (2006.01) |
| *C07K 14/00* | (2006.01) |
| *C12N 15/11* | (2006.01) |

(52) U.S. Cl.
CPC ............... *C07K 7/06* (2013.01); *A61K 38/08* (2013.01); *A61K 38/16* (2013.01); *C07K 14/00* (2013.01); *C12N 15/11* (2013.01); *A61K 38/00* (2013.01); *A61P 25/00* (2018.01)

(58) Field of Classification Search
CPC ....... C07K 7/06; C07K 14/00; C07K 14/4705; A61K 38/00; A61K 38/03; A61K 38/04; A61K 38/08; A61K 38/16
See application file for complete search history.

(56) References Cited

U.S. PATENT DOCUMENTS

| | | | |
|---|---|---|---|
| 5,618,693 A * | 4/1997 | McKnight ............ | C07K 14/705 435/252.33 |
| 2003/0157514 A1* | 8/2003 | Finger .................. | C07K 14/705 435/6.14 |
| 2011/0045009 A1* | 2/2011 | Nakagawa ........... | A61K 39/385 424/185.1 |

FOREIGN PATENT DOCUMENTS

| | | |
|---|---|---|
| CN | 1745094 A | 3/2006 |
| CN | 1849132 A | 10/2006 |
| CN | 101951942 A | 1/2011 |
| WO | 2001/013937 A1 | 3/2001 |
| WO | 2013/148331 A1 | 10/2013 |

OTHER PUBLICATIONS

"GenBank Sign in No. EKA29255, version No. EKA29255.1", [retrieve on Jan. 8, 2016 (Jan. 8, 2016)], retrieve from NCBI [online]: <www.ncbionlmonih.gov/protein/404518377>, Sep. 17, 2013 (Sep. 17, 2013), see amino acid sequence.
"GenBank Sign in No. ABU73993, version No. ABU73993.1", [retrieve on Jan. 8, 2016 (Jan. 8, 2016)], retrieve from NCBI [online]: <www.ncbionlmonih.gov/protein/156528908>, Jan. 31, 2014 (Jan. 31, 2014), see amino acid sequence.
Jonathan H. Wardman et al., ProSAAS-Derived Peptides are Colocalized with Neuropeptide Y and Function as Neuropeptides in the Regulation of Food Intake, Plos One, 2011, vol. 6, No. 12.
Jie Su et al., Identification and quantification of neuropeptides in naive mouse spinal cord using mass spectrometry reveals [des-Ser1]-cerebellin as a novel modulator of nociception, Journal of Neurochemistry, 2014, 130, 199-214.

* cited by examiner

*Primary Examiner* — Kimberly Ballard
(74) *Attorney, Agent, or Firm* — Locke Lord LLP; Tim Tingkang Xia, Esq.

(57) ABSTRACT

The present invention relates to peptides enhancing neuronal outgrowth, particularly to peptides that enhance neurite outgrowth and their application.

5 Claims, 14 Drawing Sheets
Specification includes a Sequence Listing.

US 10,407,465 B2
// 1

PEPTIDES ENHANCING NEURONAL OUTGROWTH AND APPLICATION THEREOF

BACKGROUND OF THE INVENTION

1. Field of the Invention

The present invention relates to peptides that enhance neuronal outgrowth, particularly to peptides that enhance neurite outgrowth and their application.

2. Description of the Prior Art

Learning and memory are essential abilities for human beings and other mammals. These creatures adapt to changing environments through exploring environments to gain knowledge and/or experience, then storing and integrating it in their brains, and changing minds and behaviors. Loss of memory is mainly due to continued degeneration or death of neurons and results in the failure of neural signal transmission. Adult synaptic plasticity such as neurite outgrowth, synaptic transmission, and the formation of memories is strengthened through learning and enriched environmental stimulation. Substances that promote brain neural plasticity, theoretically enhance memory formation as well. Many neurotrophic factors, including brain-derived neurotrophic factor (BDNF), glial cell-derived neurotrophic factor (GDNF), insulin-like growth factor (IGF) have been shown to promote neural plasticity as well as memory formation. However, such large proteins usually encountered structural instability, shorter half-life, and are unable to cross the blood brain barrier in vivo. Since peptides play a crucial role in physiological and biochemical functions, peptide drugs now attracted attention for their potential therapeutic use. Compared to small chemical entity drugs, peptide-based drugs possess certain favorable characteristics, including higher potency, higher selectivity, and better safety.

SUMMARY OF THE INVENTION

The first aspect of the present invention provides a peptide able to enhance neuronal outgrowth, comprising the following amino acid sequence:

$(R_1)_a$-Asn-$X_1$-$X_2$-Pro-Gln-$(R_2)_b$   (SEQ ID NO: 3)

and conservatively modified variations thereof. In the above formula, $R_1$ is an amino acid sequence comprising from 1 to about 40 amino acids, wherein each amino acid is independently selected from the group consisting of naturally occurring amino acids and amino acid analogs. With as $R_1$, $R_2$ in the above formula is an amino acid sequence comprising from 1 to about 40 amino acids, wherein each amino acid is independently selected from the group consisting of naturally occurring amino acids and amino acid analogs. $X_1$ in the above formula is an amino acid selected from the group consisting of nonpolar amino acids. $X_2$ in the above formula is an amino acid selected from the group consisting of naturally occurring amino acids and amino acid analogs. The indexes "a" and "b" in the above formula are independently selected and can be equal to zero or one.

The second aspect of the present invention provides a polynucleotide encoding any of the above peptides.

The third aspect of the present invention provides a composition comprising at least one of the above peptides and a pharmaceutically acceptable vehicle.

The fourth aspect of the present invention provides a method for enhancing neuronal outgrowth. The method comprises a step of contacting a neuronal cell with any of the above peptides in an amount sufficient to enhance neuronal outgrowth.

The fifth aspect of the present invention provides use of any one of the peptides mentioned above in the manufacture of a medicament for ameliorating the symptoms associated with neuronal cell damage or neuronal degradation in a subject.

These and other aspects of the present invention will become apparent from the following description of the preferred embodiment taken in conjunction with the following drawings, although variations and modifications therein may be effected without departing from the spirit and scope of the novel concepts of the disclosure.

BRIEF DESCRIPTION OF THE DRAWINGS

The foregoing summary, as well as the following detailed description of the invention, will be better understood when read in conjunction with the appended drawings. For the purpose of illustrating the present invention, the attached drawings illustrate some, but not all, alternative embodiments. It should be understood, however, that the invention is not limited to the precise arrangements and instrumentalities shown. These figures, which are incorporated into and constitute part of the specification, assist in explaining the principles of the invention.

FIG. 9A shows that before footshock, there was no significant difference among retention time on stage of rats in each group. FIG. 9B shows the retention time on stage 1 day after footshock. FIG. 9C shows jumping error number 1 day after footshock. The data were analyzed with one-way ANOVA, followed by a post hoc Newman-Keuls multiple-comparison tests. Data are represented as the mean±SEM. In comparison with the control group, **$p<0.01$.

FIG. 11A shows the mean escape latency (second) of each learning day before drug administration. FIG. 11B shows the mean escape latency of each learning day after 6 months of drug administration. The data were analyzed with two-way ANOVA, followed by a post hoc Newman-Keuls multiple-comparison tests. Data are represented as the mean±SEM. In comparison with the control group, *, $p<0.05$; **, $p<0.01$.

DETAILED DESCRIPTION OF THE PREFERRED EMBODIMENT

Figure 1A:
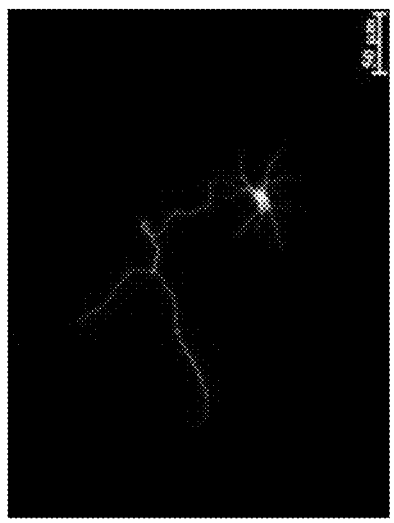
FIGS. 1A to 1I show effects of C5 peptide (SEQ ID NO: 1) and C6 peptide (SEQ ID NO: 2) on primary hippocampal neurite outgrowth. Primary hippocampal neuron cultures at 3 days in vitro (at DIV3) were treated with phosphate buffered saline (PBS, as a negative control) (FIG. 1A), C5 peptide ($10^{-9}$ M, $10^{-12}$ M, $10^{-15}$M, as shown in FIG. 1B to FIG. 1D, respectively), C6 peptide ($10^{-9}$ M, $10^{-12}$ M, $10^{-15}$M, as shown in FIG. 1F to FIG. 1H, respectively), D-form C5 peptide ($10^{-9}$ M) (FIG. 1E), or D-form C6 peptide ($10^{-12}$ M) (FIG. 1I) for 3 days, followed by immunostaining with anti-Tau anitbody (axon marker, green), anti-MAP2 antibody (dendrite marker, red), and 4',6-diamidino-2-phenylindole (DAPI, nuclear dye, blue) at 6 days in vitro (DIV6). Scale bar: 50 µm.

It should be understood that both the foregoing general description and the following detailed description are exemplary and explanatory but are not restrictive of the invention as claimed. Certain details of one or more embodiments of the invention are set forth in the description below. Other features or advantages of the present invention will be apparent from the non-exhaustive list of representative examples that follows, and also from the appending claims.

The present invention provides a peptide enhancing neuronal outgrowth, comprising the following sequence:

$(R_1)_a$-Asn-$X_1$-$X_2$-Pro-Gln-$(R_2)_b$, (SEQ ID NO: 3), and conservatively modified variations thereof; wherein $R_1$ is an amino acid sequence comprising from 1 to about 40 amino acids, wherein each amino acid is independently selected from the group consisting of naturally occurring amino acids and amino acid analogs; $R_2$ is an amino acid sequence comprising from 1 to about 40 amino acids, wherein each amino acid is independently selected from the group consisting of naturally occurring amino acids and amino acid analogs; $X_1$ is an amino acid selected from the group consisting of nonpolar amino acids; $X_2$ is an amino acid selected from the group consisting of naturally occurring amino acids and amino acid analogs; and a and b are independently selected and are equal to zero and one.

In one embodiment, a and b are both zero. In one embodiment, the peptide has a sequence of NAIPQ (SEQ ID NO: 1). In one embodiment, the peptide has a sequence of NPSPQ (SEQ ID NO: 2). In one embodiment, the peptide has a sequence of NFEPQ (SEQ ID NO: 4). In one embodiment, the peptide has a sequence of NMYPQ (SEQ ID NO: 5). In one embodiment, the peptide has a sequence of NIKPQ (SEQ ID NO: 6). In one embodiment, the peptide has a sequence of NLMPQ (SEQ ID NO: 7). In one embodiment, the peptide has a sequence of NVAPQ (SEQ ID NO: 8). In one embodiment, the peptide has a sequence of NWLPQ (SEQ ID NO: 9). The sequences listed above are exemplified, and the peptides enhancing neuronal outgrowth of the present invention are not limited to sequences of SEQ ID NOs: 1, 2, 4-9. For instance, but not limited to, when $X_1$ is alanine (Ala, A), $X_2$ can be any one of alanine, cysteine, aspartic acid, glutamic acid, phenylalanine, glycine, histidine, isoleucine, lysine, leucine, methionine, asparagine, proline, glutamine, arginine, serine, threonine, valine, tryptophan, tyrosine.

The peptides enhancing neuronal outgrowth of the present invention can be produced by, but is not limited to, a peptide synthesizer or molecular cloning. In one embodiment, the peptides are synthesized by a peptide synthesizer, and not limited to D-form or L-form. It is possible that the amino acid residues of the peptides provided in the present invention are composed of naturally occurring amino acids or unnatural amino acids known in the art, all-L or all-D, or a combination thereof. In another embodiment, the peptides can also be produced by molecular cloning. The peptides obtained by molecular cloning can be produced by, but is not limited to, inserting a polynucleotide sequence encoding one of the peptides into an expression vector to form a plasmid comprising the polynucleotide sequence encoding one of the peptides, transforming the plasmid into host cells, and inducing protein expression in the host cells to obtain the peptide enhancing neuronal outgrowth.

Therefore, the present invention also provides a polynucleotide encoding any of the above peptides, and/or a recombinant nucleic acid expression vector comprising the polynucleotide encoding any of the above peptides, and/or a host cell comprising the recombinant nucleic acid expression vector having the polynucleotide encoding any of the above peptides.

The polynucleotide sequences encoding the peptides of the present invention are derived from the amino acid sequences of the peptides enhancing neuronal outgrowth by replacing each amino acid with a three-nucleotide codon, including every degenerate codon, listed in the genetic code table. For example, each proline of the amino acid sequences of the peptides can be independently encoded by the codons CCA, CCC, CCG, or CCT.

The present invention further provides a composition comprising at least one of the above peptides and a pharmaceutically acceptable vehicle. In some embodiments, the composition has at least one of the above peptides, for instance, but is not limited to, one of NAIPQ (SEQ ID NO: 1), NPSPQ (SEQ ID NO: 2), NFEPQ (SEQ ID NO: 4), NMYPQ (SEQ ID NO: 5), NIKPQ (SEQ ID NO: 6), NLMPQ (SEQ ID NO: 7), NVAPQ (SEQ ID NO: 8), and NWLPQ (SEQ ID NO: 9), or combination thereof. In some embodiments, the composition has, but not necessarily to be, a pharmaceutically effective amount of the above peptides.

In some embodiments, the peptides of the present invention enhance neuronal outgrowth, especially increase numbers of axon branches and lengths of axons. New synapses are formed during brain activities (such as learning, memorizing, repairing, and regenerating). The process of synaptogenesis starts with formation of axonal terminal boutons in presynaptic neurons, which then triggers formation of dendritic protrusions in postsynaptic neurons. Synapses are formed by contacting of axonal terminal boutons and dendritic protrusions, so that there are cross-talk between neurons, formation of new connectivity, and brain development and remodeling to perform activities. Therefore, it is necessary to stimulate axonal growth for dendritic arborization and synapse formation to perform activities, such as learning and memorizing. Brain-derived neurotrophic factors (BDNFs) enhance neuronal outgrowth by stimulating axonal neurite outgrowth and the following dendritic arborization. Inhibitors of BDNF receptors inhibit axonal growth and cause memory loss. In some embodiments, the peptides of the present invention significantly enhance axonal growth. The role of the peptides is similar to BDNFs, in which both enhance neuronal outgrowth by increasing axonal growth.

In addition, due to few newborn new neurons are formed and continued degeneration, death, and loss of neurons in the brains of adult mammals, adults and the elderly need to rely on neurite arborization to maintain or improve cross talk between neurons. In some embodiments, the peptides of the present invention enhance neuronal outgrowth by increasing axonal growth, and thus reduce neuronal damage or neurodegeneration caused by aging or other factors, and ameliorate symptoms associated with neuronal damage or neurodegeneration in a subject.

Hence, the present invention provides a method for enhancing neuronal outgrowth, comprising contacting a neuronal cell with at least one of the above peptides in an amount sufficient to enhance neuronal outgrowth. In some embodiments, the neuronal cell is a neuronal cell with normal function. In some embodiments, the neuronal cell is a degenerated neuronal cell. In some embodiments, the neuronal cell is a damaged neuronal cell. Causes of damage or degeneration of neuronal cells include, but is not limited to, physical damage (such as mechanical damage, contusion, or cutting), chemical damage (such as damage caused by alcohol, scopolamine hydrochloride, 1-methyl-4-phenyl-6-tetrahydropyridine (MPTP), or amphetamine), biological damage (such as damage caused by cerebral hypoxia), aging or a combination thereof.

Additionally, the present invention provides a method for ameliorating memory disorders in a subject. The present invention also provides a method for ameliorating dementia in a subject. In some embodiments, memory disorders or dementia in a subject are induced by aging. In some embodiments, memory disorders or dementia in a subject are induced by mechanical injuries. In some embodiments, memory disorders or dementia in a subject are induced by chemical reagents. In some embodiments, memory disorders or dementia in a subject are induced by scopolamine hydrochloride. Scopolamine hydrochloride (Sco) is a muscarinic receptor antagonist in animals and humans, causes impairments in learning and memory. In some embodiments, the present invention uses animal model of Sco-induced amnesia to investigate the effects of the peptides disclosed in the present invention on dementia.

In some embodiments, memory disorders or dementia in a subject are induced by 1-methyl-4-phenyl-1,2,3,6-tetrahydropyridine (MPTP). MPTP is a neurotoxin precursor to 1-methyl-4-phenylpyridinium (MPP+), which causes permanent symptoms of Parkinson's disease by destroying dopaminergic neurons in the substantia nigra of the brain. In some embodiments, the present invention uses animal model of MPTP-induced Parkinson's disease to investigate the effects of the peptides disclosed in the present invention on the diseases.

In some embodiments, memory disorders or dementia in a subject are induced by natural aging or D-(+)-galactose (D-galactose). D-galactose is a nutrient under normal circumstances. However, excessive intake of D-galactose may cause non-enzymatic glycosylation (glycation), in which a sugar molecule binds to a protein or lipid molecule without the controlling action of an enzyme. Polymerization of sugar and protein with a series of reactions produces irreversible substances, which bind to other proteins and form advanced glycation end products (AGEs). Accumulation of advanced glycation end products in cells induces generation of reactive oxygen species (ROS), which lead to oxidative stress, nerve inflammation, obstruction of memory formation and synaptic transmission, neurodegeneration, and finally lead to memory deficit. This non-enzymatic glycosylation contributes to oxidative injury and aging-related diseases. From either physiological or pathological analysis, aging of rats treated with D-galactose is equivalent to 16- to 24-month old rats. In some embodiments, the present invention uses animal model of natural aging to investigate the effects of the peptides disclosed in the present invention on dementia. In some embodiments, the present invention uses animal model of D-galactose-induced aging to investigate the effects of the peptides disclosed in the present invention on dementia.

The present invention further provides use of any of the above peptides in the manufacture of a medicament for ameliorating a symptom associated with neuronal damage or neurodegeneration in a subject. In some embodiments, the symptom includes, but is not limited to, memory impairment, mental decline, coordination impairment, decline in survival rate, central nervous system lesions, Parkinson's disease, Alzheimer's disease, diseases affecting sensory neurons, limbic-cortical dysregulation, disorders associated with growth retardation and learning disabilities, Down's disease, oxidative stress-induced neuronal death, aging-associated diseases, chronic diseases and conditions related to alcohol, disorders associated with drug abuse, pathological changes in wound tissues, and conditions caused by negative side effects of the therapeutic agent and treatment. In some embodiments, the symptoms are memory impairment, mental decline, coordination impairment, decline in survival rate, Parkinson's disease, and/or Alzheimer's disease. In some embodiments, in comparison with negative controls, these symptoms are significantly improved after the subjects have been administered the peptides of the invention for a period of time.

Unless defined otherwise, all technical and scientific terms used herein have the same meanings as are commonly understood by one of skill in the art to which this invention belongs.

As used herein, the articles "a," "an," and "any" refer to one or more than one (i.e., at least one) of the grammatical object of the article. For example, "an element" means one element or more than one element.

As used herein, the term "nucleotide" refers to a monomer comprising a nitrogenous base connected to a sugar phosphate that comprises a sugar, such as ribose or 2'-deoxyribose, connected to one or more phosphate groups. "Polynucleotide" and "nucleic acid" refer to a polymer comprising more than one nucleotide monomer, in which said monomers are often connected by sugar-phosphate linkages of a sugar-phosphate backbone. A polynucleotide need not comprise only one type of nucleotide monomer. For example, the nucleotides comprising a given polynucleotide may be only ribonucleotides, only 2'-deoxyribonucleotides, or a combination of both ribonucleotides and 2'-deoxyribonucleotides. Polynucleotides include naturally occurring nucleic acids, such as deoxyribonucleic acid ("DNA") and ribonucleic acid ("RNA"), as well as nucleic acid analogs comprising one or more non-naturally occurring monomer. Polynucleotides can be synthesized, for example, using an automated DNA synthesizer. The term "nucleic acid" typically refers to large polynucleotides. It will be understood that when a nucleotide sequence is represented by a DNA sequence (i.e., A, T, G, C), this also includes an RNA sequence (i.e., A, U, G, C) in which "U" replaces "T." The term "cDNA" refers to a DNA that is complementary or identical to an mRNA, in either single stranded or double stranded form, but in which "T" replaces "U." The term "recombinant nucleic acid" refers to a polynucleotide or nucleic acid having sequences that are not naturally joined together. A recombinant nucleic acid may be present in the form of a vector.

As used herein, the term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. For the purposes of this application, the term "amino acid analogs" refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. For the purposes of this application, the term "amino acid mimetics" refers to chemical compounds that have a structure that is different from the general chemical structure of an amino acid, but that functions in a manner similar to a naturally occurring amino acid.

As used herein, the term "a nonpolar amino acid" refers to an alpha-amino acid in which the functional group attached to the alpha-carbon (i.e., R in $RCH(NH_2)COOH$)

has hydrophobic properties. The nonpolar amino acid of the present invention includes naturally occurring and synthetic nonpolar amino acids, as well as nonpolar amino acid analogs and nonpolar amino acid mimetics that function in a manner similar to the naturally occurring nonpolar amino acids; for example, but not limited to, alanine, valine, leucine, isoleucine, proline, phenylalanine, methionine, tryptophan, and alpha-aminobutyrate.

As used herein, the term "peptide" refers to a polymer of amino acid residues. The term applies to amino acid polymers in which one or more amino acid residue is an analog or mimetic of a corresponding naturally occurring amino acid, as well as to naturally occurring amino acid polymers.

As used herein, the term "conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Specifically, degenerate codon substitutions may be achieved by generating sequences in which the third position of one or more selected (or all) codons is substituted with mixed-base and/or deoxyinosine residues. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a peptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a peptide is implicit in each described sequence.

As used herein, the term "vector" refers to the means by which a nucleic acid can be introduced into a host cell to transform the host cell and facilitate expression of the nucleic acid. A vector may comprise a given nucleotide sequence of interest and a regulatory sequence. Vectors may be used for expressing the given nucleotide sequence or maintaining the given nucleotide sequence for replicating it, manipulating it, altering it, truncating it, expanding it, and/or transferring it between different locations (e.g., between different organisms or host cells or a combination thereof).

As used herein, the term "host cell" refers to single-cell prokaryotic or eukaryotic organisms including but not limited to: actinomycetes, archaea, bacteria, and yeast. A host cell may also be a single cell—including but not limited to cultured cells—from higher-order organisms such as plants and animals, including but not limited to vertebrates such as mammals and invertebrates such as insects.

As used herein, the term "conditions associated with neuronal damages or degeneration" refers to conditions (diseases and insults) leading to neuronal cell death and/or sub-lethal neuronal pathology including, for example, the following:

central nervous system disease including degenerative conditions affecting the basal ganglia (such as Huntington's disease, Wilson's disease, striatonigral degeneration, corticobasal ganglionic degeneration), Tourette's syndrome, Parkinson's disease, progressive supranuclear palsy, progressive bulbar palsy, hereditary spastic paraplegia, spinal muscular atrophy, amyotrophic lateral sclerosis, and variants thereof, dentatorubral-pallidoluysian atrophy, olivopontocerebellar atrophy, paraneoplastic cerebellar degeneration, and dopamine toxicity;

diseases affecting sensory neurons such as Friedreich's ataxia, diabetes, peripheral neuropathy, retinal neuronal degeneration;

diseases of limbic cortical systems such as cerebral amyloid angiopathy, Pick's atrophy, Retts syndrome;

neurodegenerative pathologies involving neuronal systems and/or brainstem including Alzheimer's disease, AIDS-related dementia, Leigh's disease, diffuse Lewy body disease, epilepsy, multiple system atrophy, Guillain-Barre syndrome, lysosomal storage disorders such as lipofuscinosis, late-degenerative stages of Down's syndrome, Alper's disease, vertigo as result of CNS degeneration;

pathologies associated with developmental retardation and learning impairments, Down's syndrome, and oxidative stress induced neuronal death;

pathologies arising with aging and chronic alcohol or drug abuse including, for example, with alcoholism the degeneration of neuron in locus coeruleus, cerebellum, cholinergic basal forebrain; with aging degeneration of cerebellar neurons and cortical neurons leading to cognitive and motor impairments; an with chronic amphetamine abuse degeneration of basal ganglia neurons leading to motor impairments;

pathological changes resulting from focal trauma such as stroke, focal ischemia, vascular insufficiency, hypoxic-ischemic encephalopathy, hyperglycemia, hypoglycemia, closed head trauma, or direct trauma; and pathologies arising as a negative side-effect of therapeutic drugs and treatments (e.g., degeneration of cingulate and entorhinal cortex neurons in response to anticonvulsant doses of antagonists of the NMDA (N-methyl-D-aspartate) class of glutamate receptor).

As used herein, the term "pharmaceutical composition" refers to any formulation wherein the fusion proteins or the virus-like particles of the present invention, or a combination thereof, may be formulated, stored, preserved, altered, administered, or a combination thereof. As described below, the formulation may comprise any pharmaceutically-acceptable diluent, adjuvant, buffer, excipient, carrier, or combination thereof. In general, components of the formulation are selected on the basis of the mode and route of administration, and standard pharmaceutical practice. As used herein, the term "pharmaceutical carrier" refers to any substance or combination thereof with which the fusion proteins or the virus-like particles of the present invention may be physically or chemically mixed, dissolved, suspended, or otherwise combined to yield the pharmaceutical composition of the present invention.

As used herein, the term "pharmaceutically effective amount" refers to an amount capable of or sufficient to maintain or produce a desired physiological result, including but not limited to treating, reducing, eliminating, substantially preventing, or prophylaxing, or a combination thereof, a disease, disorder, or combination thereof. A pharmaceutically effective amount may comprise one or more doses administered sequentially or simultaneously. Those skilled in the art will know to adjust doses of the present invention to account for various types of formulations, including but not limited to slow-release formulation. As used herein, the term "prophylactic" refers to a composition capable of substantially preventing or prophylaxing any aspect of a disease, disorder, or combination thereof. As used herein, the term "therapeutic" refers to a composition capable of treating, reducing, halting the progression of, slowing the progression of, beneficially altering, eliminating, or a combination thereof, any aspect of a disease, disorder, or combination thereof.

As used herein, the term "subject" refers to any individual to whom administration of the present invention is directed. A subject may be, for example, a mammal. The subject may be a human or veterinary animal, without regard to sex, age, or any combination thereof, and including fetuses. A subject may optionally be afflicted with, at risk for, or a combination thereof a particular disease, disorder, or combination thereof.

Formulations suitable for administration of the present invention may comprise, possibly among other things well known to those of skill in the art: aqueous and non-aqueous solutions, antioxidants, bacteriostats, buffers, solutes that affect isotonicity, preservatives, solubilizers, stabilizers, suspending agents, thickening agents, or a combination thereof.

In addition or in the alternative, formulations suitable for administration of the present invention may comprise, possibly among other things well known to those of skill in the art: gels, PEG such as PEG 400, propylene glycol, saline, sachets, water, other appropriate liquids known in the art, or a combination thereof.

Also in the addition or in the alternative, formulations suitable for administration of the present invention may comprise, possibly among other things well known to those of skill in the art: binders, buffering agents, calcium phosphates, cellulose, colloids, such as colloidal silicon dioxide, colorants, diluents, disintegrating agents, dyes, fillers, flavoring agents, gelatin, lactose, magnesium stearate, mannitol, microcrystalline gelatin, moistening agents, paraffin hydrocarbons, pastilles, polyethylene glycols, preservatives, sorbitol, starch, such as corn starch, potato starch, or a combination thereof, stearic acid, sucrose, talc, triglycerides, or a combination thereof.

Also in addition or in the alternative, formulations suitable for administration of the present invention may comprise, possibly among other things well known to those of skill in the art: alcohol such as benzyl alcohol or ethanol, benzalkonium chloride, buffers such as phosphate buffers, acetate buffers, citrate buffers, or a combination thereof, carboxymethylcellulose or microcrystalline cellulose, cholesterol, dextrose, juice such as grapefruit juice, milk, phospholipids such as lecithin, oil such as vegetable, fish, or mineral oil, or a combination thereof, other pharmaceutically compatible carriers known in the art, or a combination thereof.

Also in the addition or in the alternative, formulations suitable for administration of the present invention may comprise, possibly among other things well known to those of skill in the art: biodegradables such as poly-lactic-coglycolic acid (PLGA) polymer, other entities whose degradation products can quickly be cleared from a biological system, or a combination thereof.

Formulations of the present invention may be administered in unit-dose form, multi-dose form, or a combination thereof. They may be packaged in unit-dose containers, multi-dose containers, or a combination thereof. The present invention may exist in ampoules, cachets, capsules, granules, lozenges, powders, tablets, vials, emulsions, including but not limited to acacia emulsions, suspensions, or a combination thereof.

The present invention is further illustrated by the following examples, which are provided for the purpose of demonstration rather than limitation. Those of skill in the art should, in light of the present disclosure, appreciate that many changes can be made in the specific embodiments which are disclosed and still obtain a like or similar result without departing from the spirit and scope of the invention.

EXAMPLE

Example 1

Effects of C5 Peptide, C6 Peptide, P1 Peptide, P2 Peptide, P3 Peptide, P4 Peptide, P5 Peptide, and P6 Peptide on Neuronal Outgrowth 1. Peptide Preparation Both D-form and L-form of C5, C6, P1, P2, P3, P4, P5, and P6 peptides were synthesized by a peptide synthesizer (Neogene Biomedicals Corp., Taipei, Taiwan). The synthesized C5 peptide (SEQ ID NO: 1), C6 peptide (SEQ ID NO: 2), P1 peptide (SEQ ID NO: 4), P2 peptide (SEQ ID NO: 5), P3 peptide (SEQ ID NO: 6), P4 peptide (SEQ ID NO: 7), P5 peptide (SEQ ID NO: 8), and P6 peptide (SEQ ID NO: 9) were dissolved in DMSO and in PBS, respectively.

2. Cell Culture

In order to culture embryonic hippocampal primary neurons, pregnant Sprague-Dawley rats were purchased from the National Laboratory Center in Taiwan (Taipei, Taiwan). The hippocampal tissue from the embryos of the Sprague-Dawley rats (embryonic day 19, E19) was dissociated with enzyme and plated onto poly-L-lysine-coated coverslips with a minimal essential medium containing 5% calf serum, 5% horse serum, and 50 ng/mL insulin-transferrin-selenite (Sigma-Aldrich, St. Louis, Mo., USA). After plating, the medium was replaced with 2% of B27-neurobasal medium (Invitrogen, Carlsbad, Calif., USA) containing 0.5 mM glutamine and 12.5 mM glutamate. Embryonic hippocampal primary neurons were incubated at 37° C., 5% $CO_2$ for further experimental treatment.

3. Neuronal Outgrowth Assay

Primary hippocampal neuron cultures at 3 days in vitro (at DIV3) were treated with $10^{-9}$ M, $10^{-12}$M, $10^{-15}$ M C5 peptide (L-form), $10^{-9}$ M, $10^{-12}$M, $10^{-15}$ M C6 peptide (L-form), $10^{-9}$ M P1 peptide (L-form), $10^{-9}$ M P2 peptide (L-form), $10^{-9}$ M P3 peptide (L-form), $10^{-9}$ M P4 peptide (L-form), $10^{-9}$ M P5 peptide (L-form), $10^{-9}$ M P6 peptide (L-form), $10^{-9}$ M C5 peptide (D-form), and $10^{-12}$ C6 peptide (D-form), respectively, for 3 days, followed by immunocytochemistry. Embryonic hippocampal primary neurons of negative control were treated with PBS. Each treatment condition was run in 3 replicates.

4. Immunocytochemistry

Cultured hippocampal neurons were fixed with 4% paraformaldehyde and permeablized with 0.1% Triton X-100 at room temperature (RT). Cultures were then incubated in the primary rabbit anti-Tau antibody (a selective marker for axons, Millipore, Mass., USA) and the primary mouse anti-MAP2 antibody (microtubule-associated protein-2, which is a selective marker for dendrites, Millipore) for 1 hour at RT. After wash, cells were incubated with Alexa Fluor® 488 goat anti-rabbit secondary antibody (green fluorescence, Abcam Plc., UK) and Alexa Fluor® 594 goat anti-mouse secondary antibody (red fluorescence, Abcam Plc.) for 1 hour at RT. Then, nuclei were stained with 4',6-diamidino-2-phenylindole (DAPI, blue fluorescence, Vector Laboratories, USA). After that, coverslips were mounted on the cells, and images were obtained by using an Axio Observer D1 microscope (Zeiss, Jena, Germany) and analyzed by ImageJ software (Inage Processing and Analysis in Java, National Institutes of Health, USA). Neuronal process longer than 10 μm is defined as a neurite.

5. Statistical Analysis

The biochemical data were analyzed with one-way analysis of variance (one way ANOVA), followed by a post hoc Newman-Keuls multiple-comparison test.

6. Results

Figure 1B:
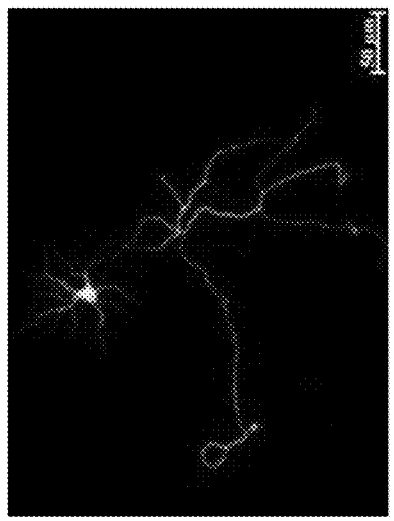
Figure 1C:
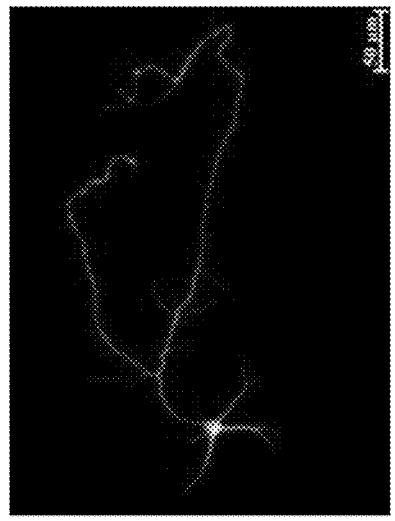
Figure 1D:
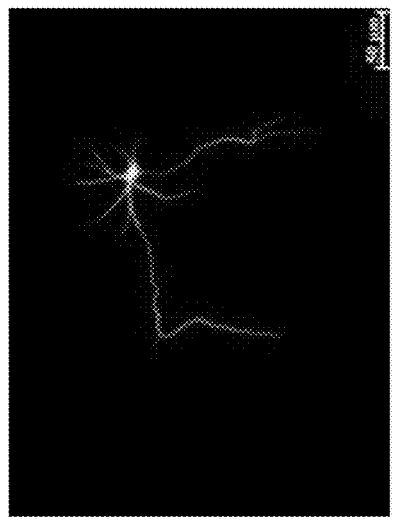
Figure 1E:
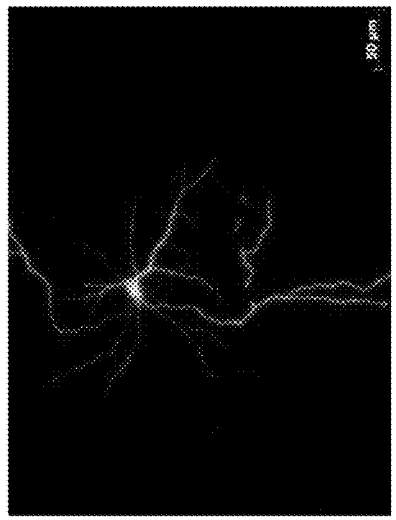
Figure 1F:
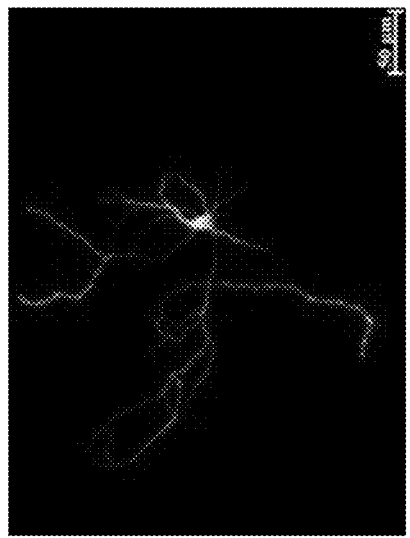
Figure 1G:
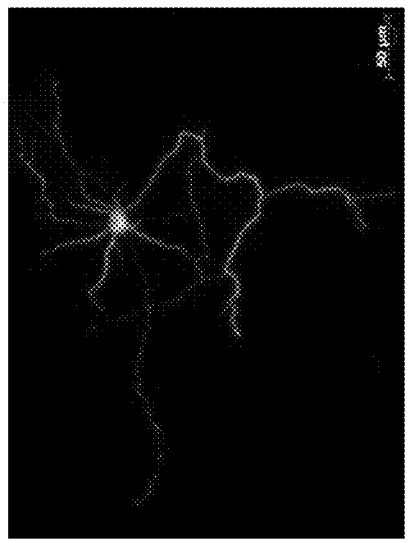
Figure 1H:
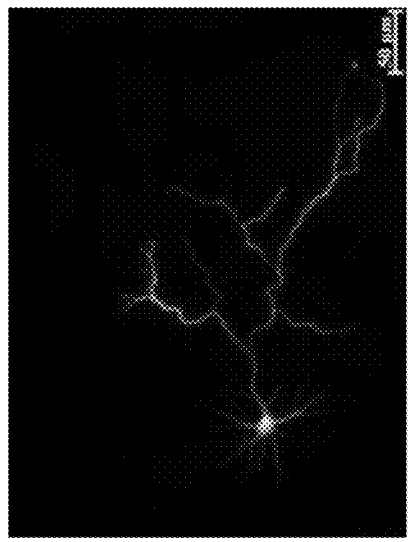
Figure 1I:
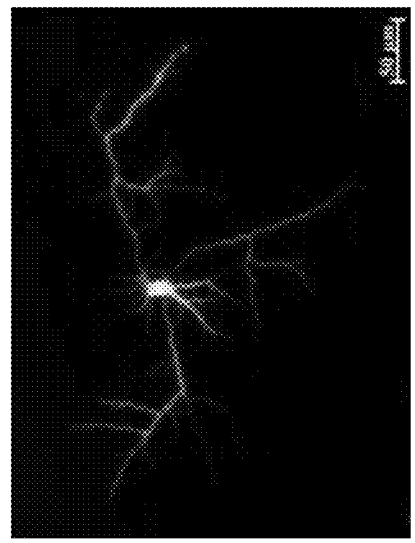
Figure 2A:
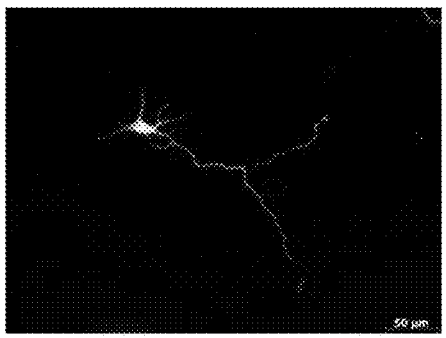
FIGS. 2A to 2G show effects of P1 peptide (SEQ ID NO: 4), P2 peptide (SEQ ID NO: 5), P3 peptide (SEQ ID NO: 6), P4 peptide (SEQ ID NO: 7), P5 peptide (SEQ ID NO: 8), and P6 peptide (SEQ ID NO: 9) on primary hippocampal neurite outgrowth. Primary hippocampal neuron cultures at 3 days in vitro (at DIV3) were treated with PBS (as a negative control, FIG. 2A), P1 peptide ($10^{-9}$ M, FIG. 2B), P2 peptide ($10^{-9}$ M, FIG. 2C), P3 peptide ($10^{-9}$ M, FIG. 2D), P4 peptide ($10^{-9}$ M, FIG. 2E), P5 peptide ($10^{-9}$ M, FIG. 2F), or P6 peptide ($10^{-9}$ M, FIG. 2G) for 3 days, followed by immunostaining with anti-Tau anitbody (axon marker, green), anti-MAP2 antibody (dendrite marker, red), and 4',6-diamidino-2-phenylindole (DAPI, nuclear dye, blue) at 6 days in vitro (DIV6). Scale bar: 50 µm.
Figure 2B:
Figure 2C:
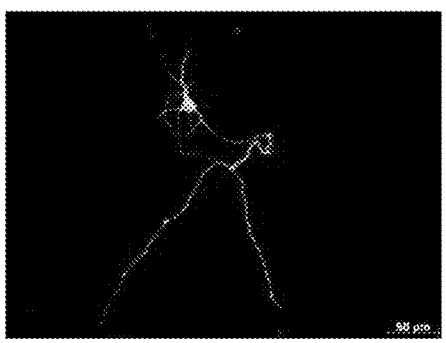
Figure 2D:
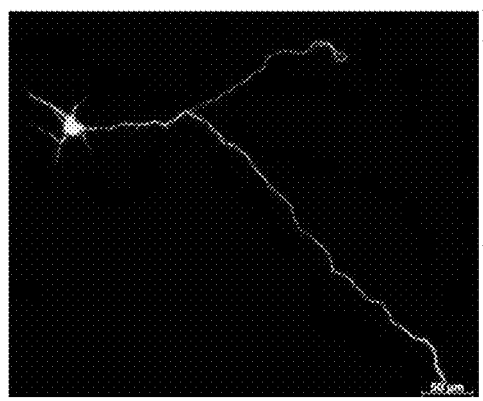
Figure 2E:
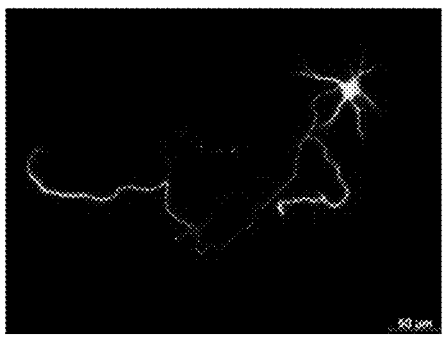
Figure 2G:
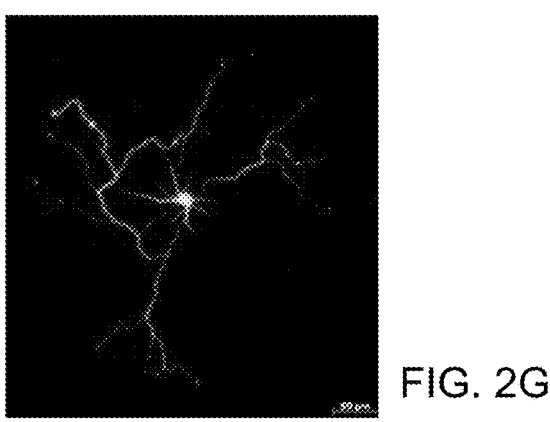
Figure 2F:
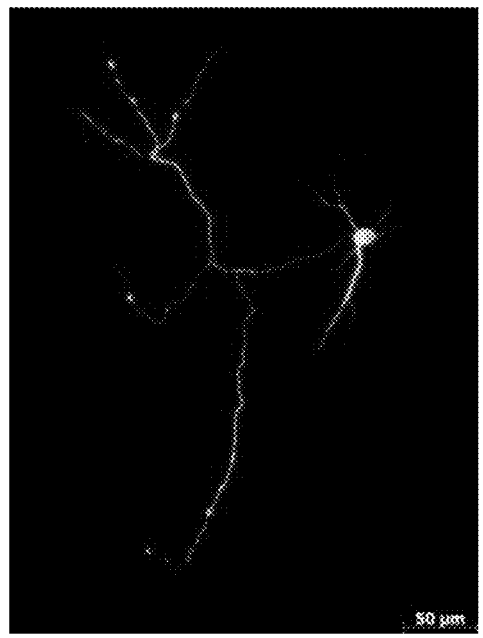

All of C5 peptide, C6 peptide, P1 peptide, P2 peptide, P3 peptide, P4 peptide, P5 peptide, and P6 peptide enhance neuronal outgrowth and branch formation. The immunocytochemistry results are shown in FIGS. 1 and 2. As shown in FIGS. 1A to 1I, compared with the negative control group (FIG. 1A), treatment of C5 peptide ($10^{-9}$ M, $10^{-12}$ M, $10^{-15}$ M) (as shown in FIGS. 1B, 1C, and 1D, respectively) or C6 peptide ($10^{-9}$ M, $10^{-12}$ M, $10^{-15}$ M) (as shown in FIGS. 1F, 1G, and 1H, respectively) at 3 DIV for 3 days enhanced axon outgrowth. In addition to the naturally occurring L-form C5 and C6 peptides, synthetic D-form C5 peptide ($10^{-9}$ M) and D-form C6 peptide ($10^{-12}$ M) exerted similar effect on neurite outgrowth, respectively (as shown in FIGS. 1E and 1I). Furthermore, as shown in FIGS. 2A to 2G, compared with the negative control group (FIG. 2A), treatment of $10^{-9}$ M P1 peptide, P2 peptide, P3 peptide, P4 peptide, P5 peptide, or P6 peptide (as shown in FIGS. 2B, 2C, 2D, 2E, 2F, and 2G, respectively) at 3 DIV for 3 days enhanced axon outgrowth.

Figure 3A:
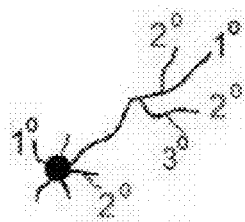
FIGS. 3A to 3E show statistical results of numbers and lengths of axon branches of the primary hippocampal neurons after treatment of some exemplified peptides of the present invention. A diagram of neuron branches is shown in FIG. 3A. Primary hippocampal neuron cultures at 3 days in vitro (at DIV3) were treated with C5 peptide ($10^{-12}$ M) or C6 peptide ($10^{-12}$ M) for 3 days, followed by immunostaining with anti-Tau antibody (green), anti-MAP2 antibody (red) and DAPI (blue), and then numbers (FIG. 3C) and length (FIG. 3B) of axon branches were counted. In addition, primary hippocampal neuron cultures at 3 days in vitro (at DIV3) were treated with P1 peptide ($10^{-9}$ M), P2 peptide ($10^{-9}$ M), P3 peptide ($10^{-9}$ M), P4 peptide ($10^{-9}$ M), P5 peptide ($10^{-9}$ M), or P6 peptide ($10^{-9}$ M) for 3 days, followed by immunostaining with anti-Tau antibody (green), anti-MAP2 antibody (red) and DAPI (blue), and then numbers (FIG. 3E) and length (FIG. 3D) of axon branches were counted. Data were analyzed by Image J software and One-way ANOVA, followed by Newman-Keuls test. Data are represented as the mean±SEM. In comparison with the control group, **, $p<0.01$.

In addition, the number and length of axon branches were counted, and the statistic results are shown in FIGS. 3B to 3E. An axon extending from the cell body of a neuron is defined as a first order axon branch; an axon extending from a first order axon branch is defined as a second order axon branch, and an axon extending from a second order axon branch is defined as a third order axon branch, et cetera (FIG. 3A). Only axons longer than 10 μm are counted.

Figure 3B:
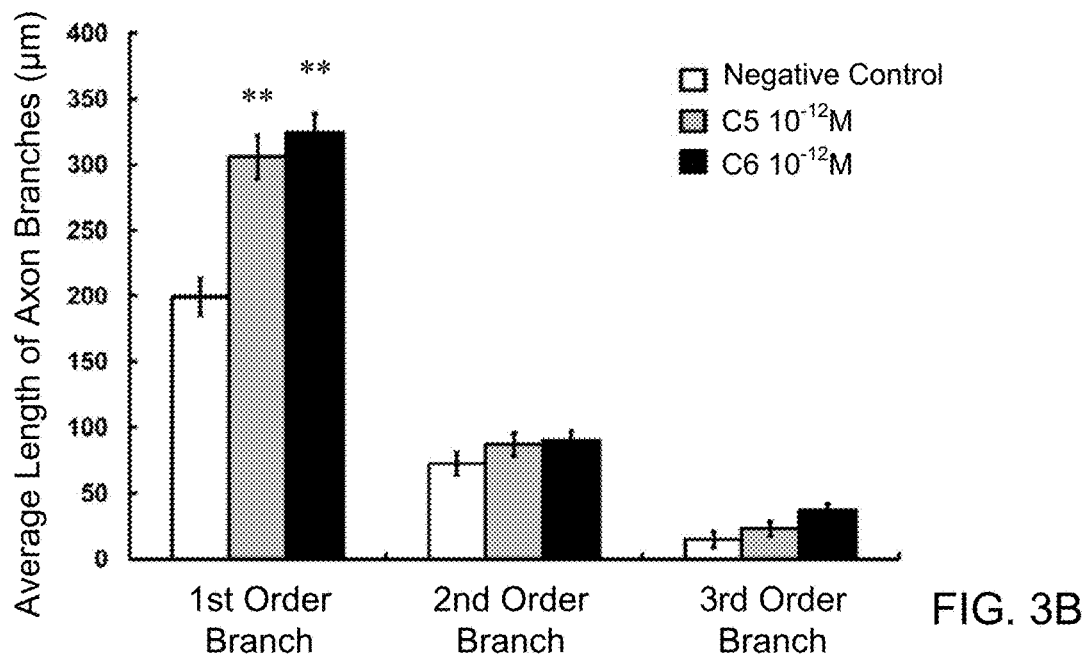
Figure 3C:
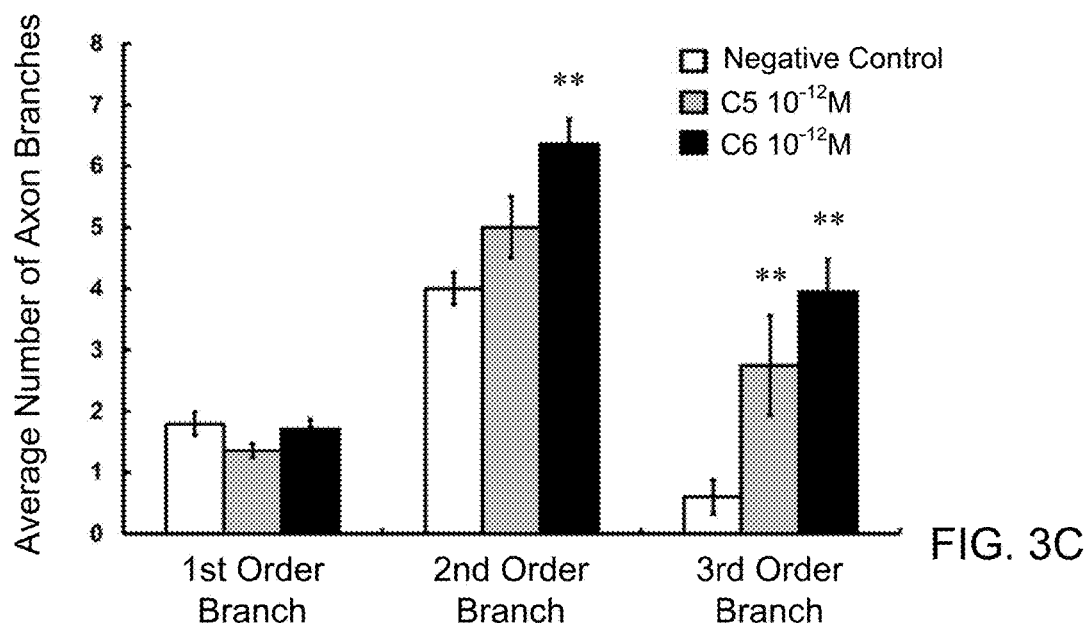

FIG. 3B shows lengths of axon branches after treatment of C5 peptide or C6 peptide. Compared to the first order axon branches of hippocampal neurons without treatment of C5 peptide or C6 peptide (negative control), the first order axon branches of hippocampal neurons treated with C5 peptide ($10^{-9}$ M) or C6 peptide ($10^{-9}$ M) are longer. This result indicates that both C5 peptide and C6 peptide significantly increase lengths of the first order axon branches of hippocampal neurons ($p<0.01$). Furthermore, FIG. 3C shows numbers of axon branches after treatment of C5 peptide or C6 peptide. The average number of third order axon branches of hippocampal neurons without treatment of C5 peptide or C6 peptide (negative control) is 0.7, whereas the average number of third order axon branches of hippocampal neurons treated with C5 peptide ($10^{-9}$ M) or C6 peptide ($10^{-9}$ M) are 3 and 4.9, respectively. In addition, the average number of second order axon branches of hippocampal neurons without treatment of C5 peptide or C6 peptide (negative control) is 4.3, whereas the average number of second order axon branches of hippocampal neurons treated with C6 peptide ($10^{-9}$ M) is 6.5. The results indicate that both C5 peptide and C6 peptide significantly increase numbers of axon branches of hippocampal neurons ($p<0.01$).

Figure 3D:
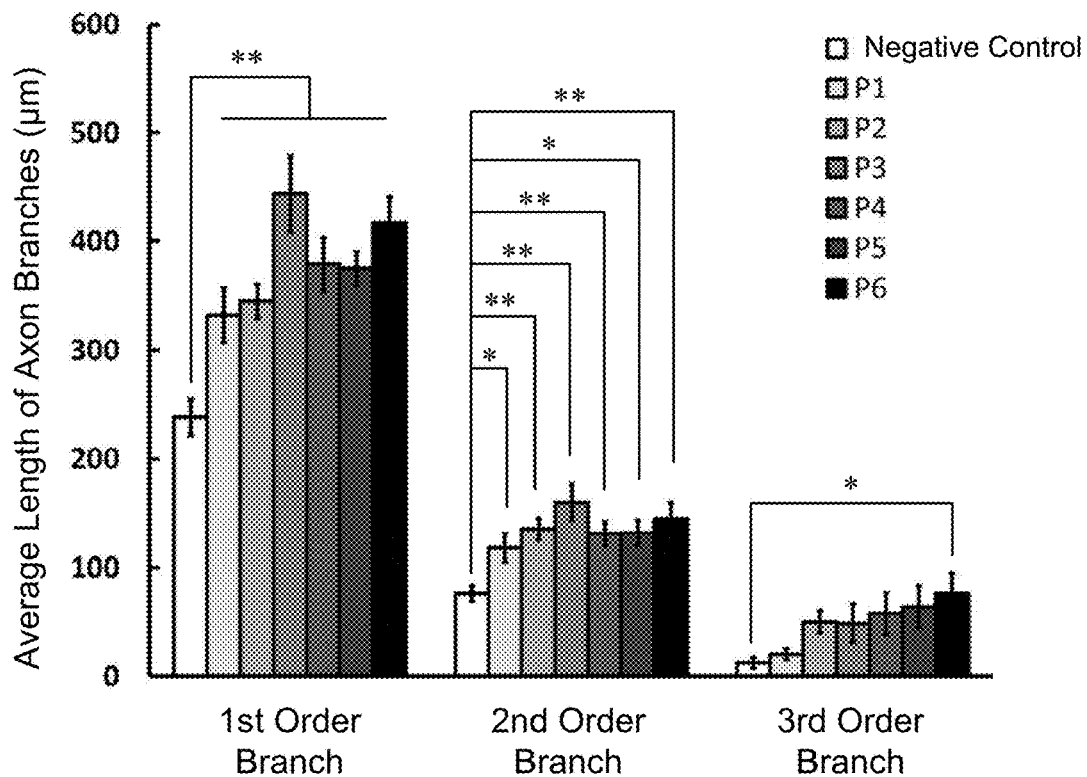
Figure 3E:
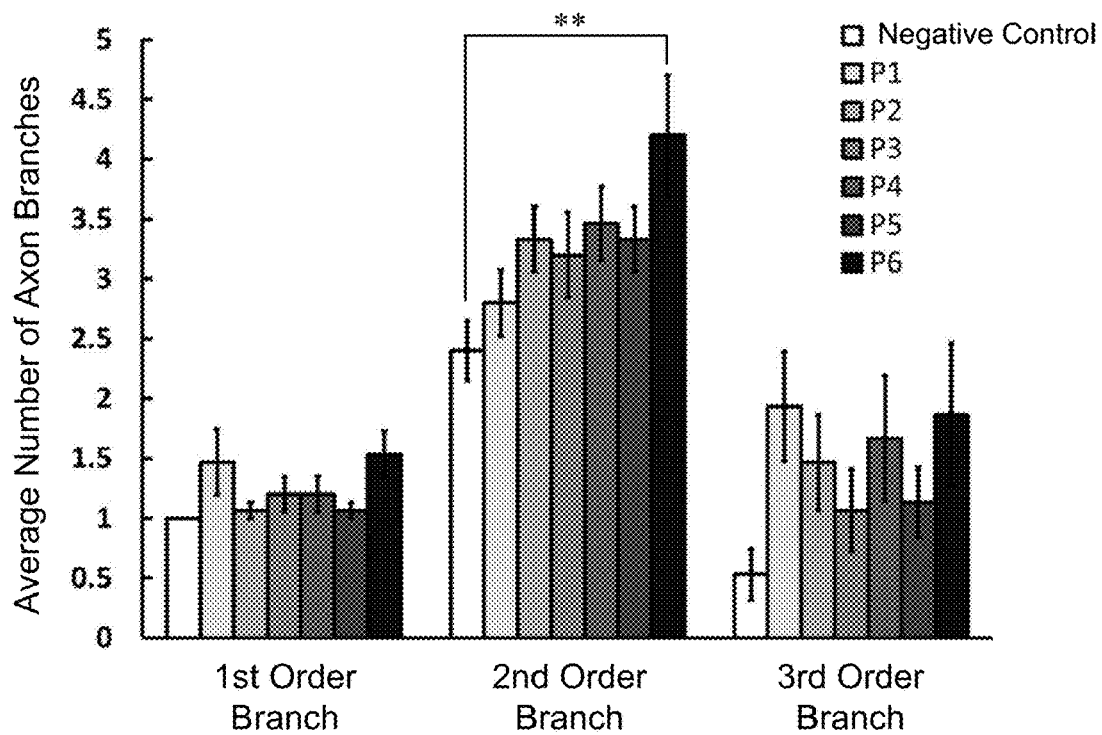

FIG. 3D shows lengths of axon branches after treatment of P1 peptide, P2 peptide, P3 peptide, P4 peptide, P5 peptide, or P6 peptide. Compared to the first and second order axon branches of the hippocampal neurons of negative control, the first and second order axon branches of hippocampal neurons treated with P1 peptide, P2 peptide, P3 peptide, P4 peptide, P5 peptide, or P6 peptide ($10^{-9}$ M) are longer. This result indicates that all of P1 peptide, P2 peptide, P3 peptide, P4 peptide, P5 peptide, and P6 peptide significantly increase lengths of the first and second order axon branches of hippocampal neurons ($p<0.01$ or $p<0.05$). In addition, compared to the third order axon branches of the hippocampal neurons of negative control, the third order axon branches of hippocampal neurons treated with P6 peptide ($10^{-9}$ M) are significantly longer ($p<0.05$). Furthermore, FIG. 3E shows numbers of axon branches after treatment of P1 to P6 peptides. The average number of second order axon branches of the hippocampal neurons of negative control is 2.5, whereas the average number of second order axon branches of hippocampal neurons treated with P6 peptide ($10^{-9}$ M) is 4.2. The result indicates that P6 peptide significantly increases numbers of axon branches of hippocampal neurons ($p<0.01$).

Example 2

Analyses of Neurotoxicity of C5 Peptide and C6 Peptide on Primary Neuron Culture 1. Materials C5 peptide, C6 peptide, and embryonic hippocampal primary neurons were prepared by the methods described in Example 1.

2. Cell Treatment

At the first day in vitro (1 DIV), embryonic hippocampal primary neurons were treated with $10^{-3}$ M, $10^{-6}$ M, $10^{-9}$ M, $10^{-12}$ M C5 peptide or C6 peptide, respectively, for 24 hours, followed by cell viability assay.

3. Cell Viability Assay

Cell viability was evaluated by an MTT (3-(4,5-cimethylthiazol-2-yl)-2,5-diphenyl tetrazolium bromide) assay. Cells were incubated with an MTT reagent (0.5 mg/mL, Sigma-Aldrich, USA) at 37° C. for 1 hour. The MTT solution was removed, and DMSO was added to the wells shaken at room temperature for 1 hour. The amount of MTT formazan product was quantified by measuring its absorbance at 570 and 630 nm by using an ELISA plate reader (SpectraMax M2 Microplate Readers, Molecular Devices, Sunnyvale, Calif., USA).

4. Statistical Analysis

The biochemical data were analyzed with one-way analysis of variance (one way ANOVA), followed by a post hoc Newman-Keuls multiple-comparison test.

5. Results

Figure 4:
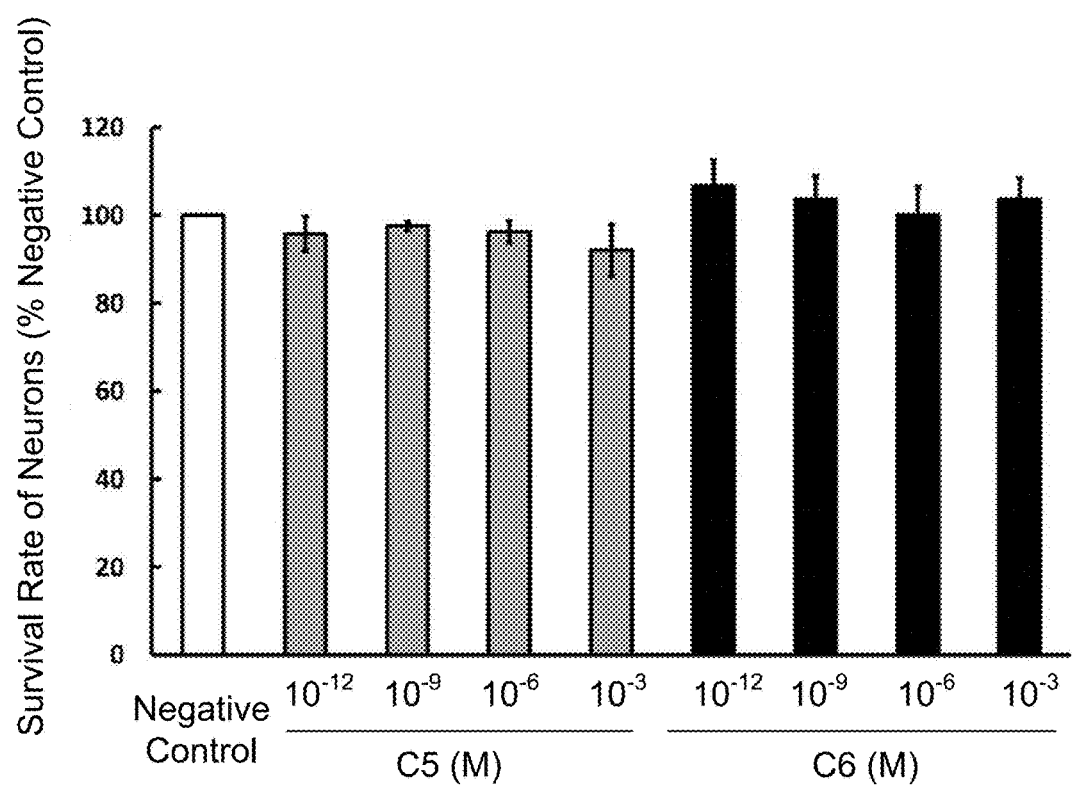
FIG. 4 shows effects of different concentrations of C5 peptide ($10^{-12}$ M, $10^{-9}$ M, $10^{-6}$ M, $10^{-3}$ M) and C6 peptide ($10^{-12}$ M, $10^{-9}$ M, $10^{-6}$ M, $10^{-3}$ M) on viability of primary hippocampal neuron by an MTT assay. Data are represented as the mean±SEM from 3 samples.

Neither C5 peptide nor C6 peptide exhibits neurotoxicity on primary neuron culture. Results of MTT assay are shown in FIG. 4. Embryonic hippocampal primary neurons were treated with $10^{-3}$ M, $10^{-6}$ M, $10^{-9}$ M, $10^{-12}$ M C5 peptide or C6 peptide, respectively, for 24 hours. C5 peptide and C6 peptide showed no significant neurotoxic effect on the embryonic hippocampal primary neurons ($p>0.05$).

Example 3

Effects of C5 Peptide and C6 Peptide on Regeneration of Primary Hippocampal Neurons 1. Materials C5 peptide, C6 peptide, and embryonic hippocampal primary neurons were prepared by the methods described in Example 1.

2. Scratch Test

The scratch test was use to evaluate the effect of C5 peptide and C6 peptide in neuronal regeneration. Embryonic hippocampal primary neurons were cultured to 5 days in vitro (DIV5). A scratch test was conducted. A tip was used to mark a cross at the wells of the plate. Culture medium containing $10^{-9}$ M C5 peptide or $10^{-9}$ M C6 peptide was added to the plate. After the neurons were incubated for 72 hours, immunofluorescence staining was conducted.

3. Immunocytochemistry

The method of immunocytochemistry is described in Example 1. Cultured hippocampal neurons were incubated in the primary rabbit anti-Tau antibody (a selective marker for axons, Millipore) followed by incubating with Alexa Fluor® 488 goat anti-rabbit secondary antibody (green fluorescence, Abcam Plc., UK). Then, nuclei were stained with DAPI (blue fluorescence, Vector Laboratories). Images of cells were obtained by using an Axio Observer D1 microscope (Zeiss, Jena, Germany) and analyzed by ImageJ software (Inage Processing and Analysis in Java, National Institutes of Health, USA).

4. Statistical Analysis.

The biochemical data were analyzed with one-way analysis of variance (one way ANOVA), followed by a post hoc Newman-Keuls multiple-comparison test.

5. Results

Figure 5A:
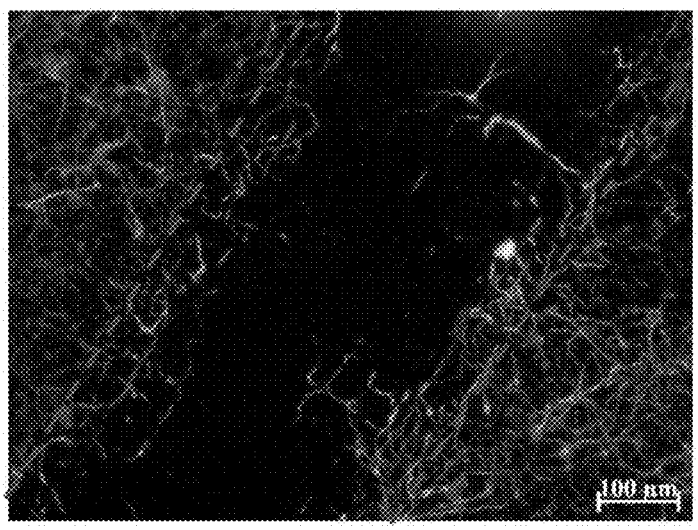
FIGS. 5A to 5C show effects of C5 peptide and C6 peptide on regeneration of primary hippocampal neurons. At 5 days in vitro (DIV5), embryonic hippocampal primary neurons were subjected to mechanical scratch lesion. The scratched embryonic hippocampal primary neurons were then treated with PBS (FIG. 5A), C5 peptide ($10^{-9}$ M) (FIG. 5B), and C6 peptide ($10^{-9}$ M) (FIG. 5C), respectively, for 96 hours, followed by immunostaining with anti-Tau anitbody (green, axon marker) and DAPI (blue, nucleus dye). Scale bar: 100 μm.
Figure 5B:
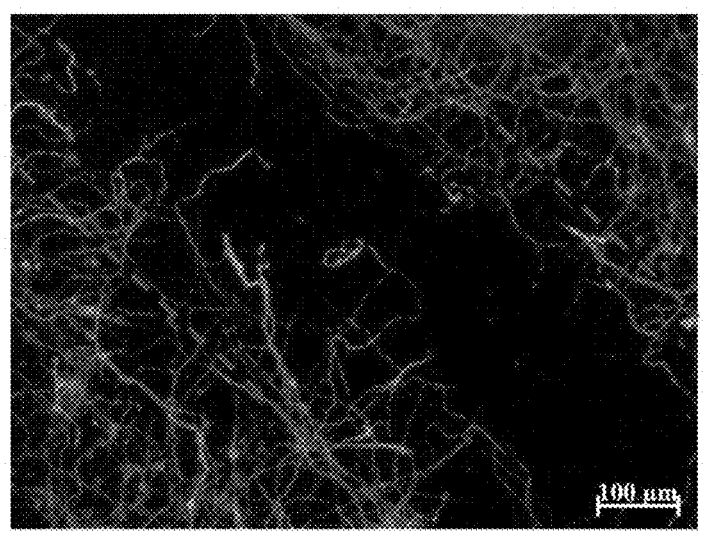
Figure 5C:
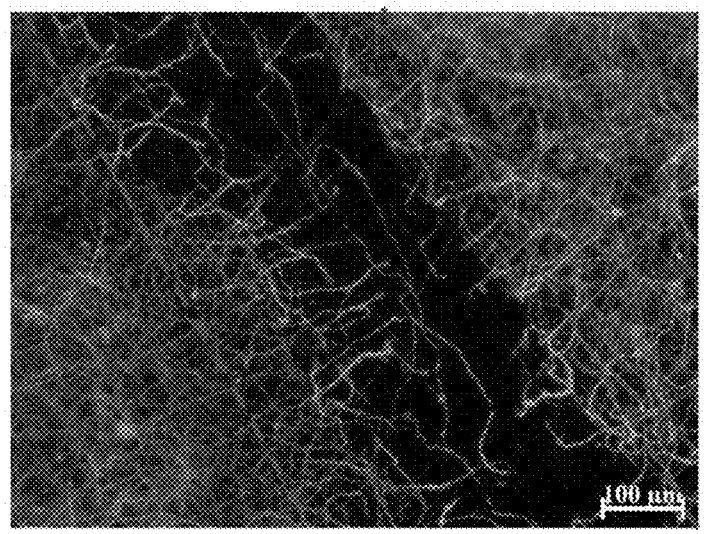

Both C5 peptide and C6 peptide enhance axon regeneration. The results of scratch assay are shown in FIG. 5. Scratched embryonic hippocampal primary neurons treated with PBS (negative control) had few axons growing across the scratch borders (FIG. 5A), whereas scratched embryonic hippocampal primary neurons treated with C5 peptide or C6 peptide had more and longer axons growing across the scratch borders (FIGS. 5B and 5C). The results indicate that C5 peptide and C6 peptide improve neurite regeneration after scratch lesion.

Example 4

Effects of C5 Peptide and C6 Peptide on Spatial Learning and Memory—Water Maze Task 1. Animals.

Adult male Sprague-Dawley rats (300-400 g) were purchased from the National Laboratory Center in Taiwan. Rats were housed (2 per cage) in a temperature (22-24° C.) and humidity (50%-60%)-controlled room at the Animal Facility of Ilan University (Taiwan). Animals were housed in a room maintained on a 12 h/12 h light/dark cycle with food and water available ad libitum. Animals were allowed to acclimatize to the room for 1 week before any experimental procedure was conducted. All experimental procedures were approved by the Guide for the Care and Use of Laboratory Animals, by the National Institutes of Health (NIH Publications No. 8023, revised 1978), and were performed by people who had received the appropriate training by the National Laboratory Center in Taiwan. All experiments were also approved by the Ethical Committee of Animal Experimentation at Ilan University.

2. Materials

C5 peptide and C6 peptide were prepared by the methods described in Example 1.

3. Drug Treatment

Twenty-five (25) adult male naïve Sprague-Dawley rats were randomly divided into 5 groups of 5 rats each. Rats in the 5 groups were intraperitoneally injected with low dose of C5 peptide (54 µg/kg), high dose of C5 peptide (270 µg/kg), low dose of C6 peptide (5.4 µg/kg), high dose of C6 peptide (27 µg/kg), and 0.5% (v/v) DMSO/PBS (negative control), respectively. The injection volume was 1 µL/g of body weight, and the injection program started on 14 days prior to behavioral experiments and continued through the experimentation.

4. Water Maze Learning

A plastic circular pool 183 cm in diameter was filled with water (25±2° C.). A circular platform was placed at a specific location from the edge of the pool and submerged below the water surface. Water was made cloudy by adding toxic-free dye. Distinctive visual cues were set on the wall. For spatial learning, animals were subjected to 3 trials per day, with one trial early in the morning, one trial at noon, and another in the late afternoon. The training procedure lasted 4 days, and a total of 12 trials were given. The rats were positioned at different starting points spaced equally around the perimeter of the pool in random order. They had 60 seconds to swim in the pool. If a rat could not find the platform, it was guided to the platform and was allowed to remain there for 20 seconds. The time each animal took to reach the platform was recorded as the escape latency. A probe trial of 60 seconds was given on Day 5 to test their memory retention. The rats were placed in the pool with the platform removed, and the time they spent in each quadrant (Quadrants 1, 2, 3, and 4) was recorded. The longer a rat stayed in the target quadrant (quadrant 4), the better memory the rat had. At the end of the experiment, the rats were subjected to visible platform learning. For visible platform learning, a flag was mounted on the platform, and the platform was raised above the surface of the water. The time the rats found the platform was recorded. In addition, no dye was added in the pool, so that the animals could see the location of the platform from the water.

5. Statistical Analysis.

The data were analyzed with two-way ANOVA, followed by a post hoc Newman-Keuls multiple-comparison tests.

6. Results

Figure 6:
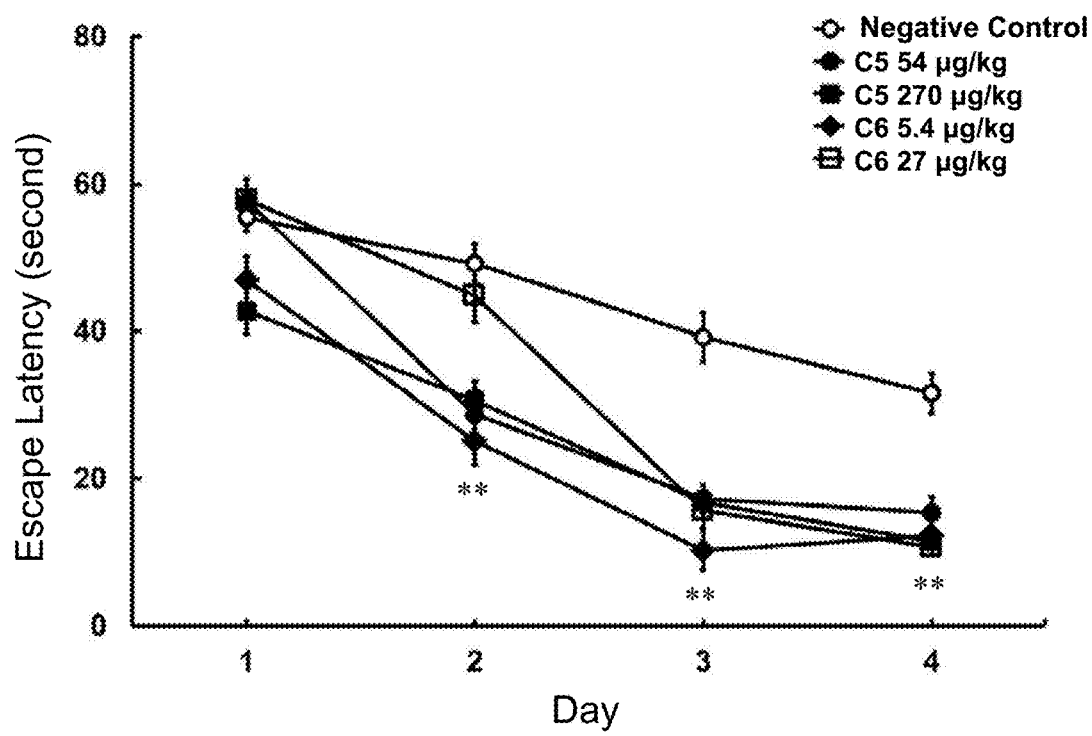
FIG. 6 shows investigation of effects of C5 peptide and C6 peptide on spatial learning and memory by water maze task. Spraque-Dawley (SD) rats were randomly divided into control, C5 low dose group (54 μg/kg), C5 high dose group (270 μg/kg), C6 low dose group (5.4 μg/kg), and C6 high dose group (27 μg/kg). Escape latency (second) of each water-maze learning day was recorded. The data were analyzed with two-way ANOVA, followed by a post hoc Newman-Keuls multiple-comparison tests. Data are represented as the mean±SEM. In comparison with the control group, **, $P<0.01$.

Both C5 peptide and C6 peptide enhance spatial learning and memory in rats. FIG. 6 shows the average escape latency (second) of each group of rats in each water-maze learning day. Compared to rats receiving 0.5% (v/v) DMSO/PBS (negative control), rats receiving C5 peptide (54 µg/kg, 270 µg/kg) and C6 peptide (5.4 µg/kg, 27 µg/kg) spent significantly less time finding the hidden platform [$F(4.20)=15.168$, $p<0.01$]. The results indicate that C5 peptide and C6 peptide enhance spatial learning and memory in rats.

Example 5

Effects of C5 Peptide and C6 Peptide on Scopolamine-Induced Spatial Learning and Memory Deficits—Water Maze Task 1. Animals.

Rats were obtained and taken care of as described in Example 4.

2. Materials

C5 peptide and C6 peptide were prepared by the methods described in Example 1. Scopolamine hydrochloride (Sco) was purchased from Sigma-Aldrich Co. (St. Louis, Mo., USA). Sco was dissolved in saline to a final concentration of 1.5 mg/mL for further use.

3. Drug Treatment

Sprague-Dawley rats were randomly divided into negative control group, scopolamine-injected group (Sco), C5 peptide and scopolamine-injected group (C5+Sco), and C6 peptide and scopolamine-injected group (C6+Sco), and rats in the 4 groups were intraperitoneally injected with vehicle (to negative control group and scopolamine only group), C5 peptide (54 µg/kg/day, C5+Sco group), and C6 peptide (5.4 µg/kg/day, C6+Sco group), respectively, for 14 consecutive days. After that, rats in the 4 groups were intraperitoneally injected with vehicle (negative control group), vehicle and scopolamine (1.5 mg/kg/day)(scopolamine only group), C5 peptide (54 µg/kg/day) and scopolamine (1.5 mg/kg/day) (C5+Sco group), and C6 peptide (5.4 µg/kg/day) and scopolamine (1.5 mg/kg/day) (C6+Sco group), respectively, for 7 consecutive days. Then, behavioral experiments were conducted, and the injection program with scopolamine continued through the experimentation. The injection volume was 1 µL/g of body weight. The scopolamine injection was performed 30 minutes before behavioral experiments every morning, and the C5 peptide or C6 peptide injection was conducted once daily at 5:00 PM 1 day prior.

4. Water Maze Learning

Method of water maze learning is described in Example 4.

5. Statistical Analysis

The data were analyzed with two-way ANOVA, followed by a post hoc Newman-Keuls multiple-comparison tests.

6. Results

Figure 7:
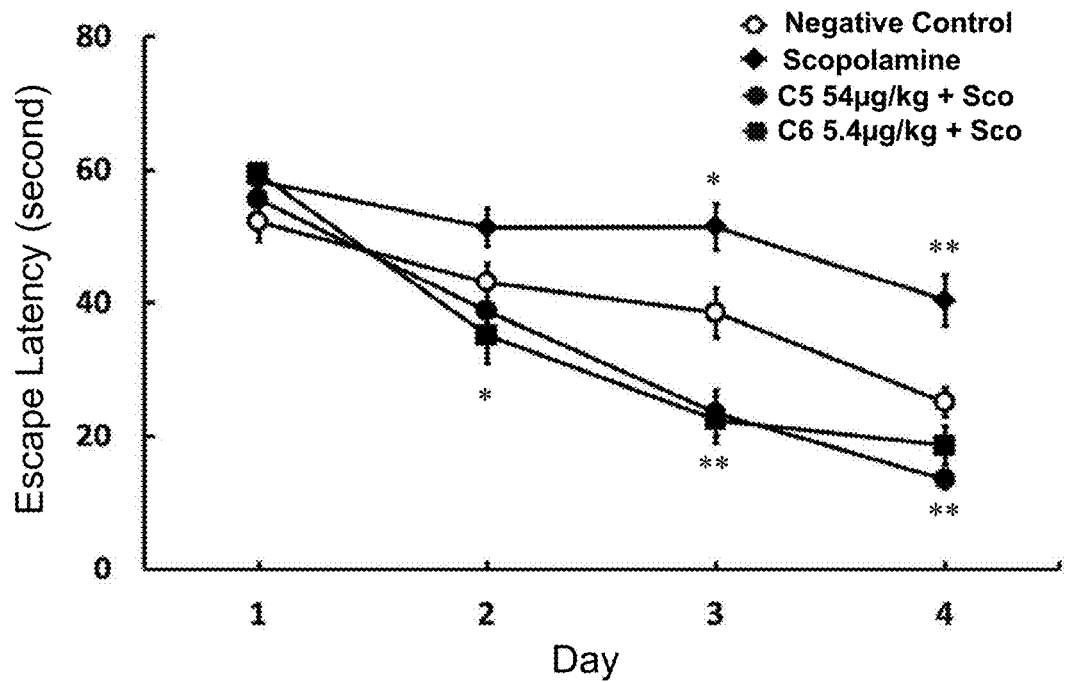
FIG. 7 shows effect of C5 peptide and C6 peptide on scopolamine-induced memory impairment in water maze memory formation in rats. Rats were randomly divided into negative control, scopolamine-injected group (Sco), C5 peptide and scopolamine-injected group (C5+Sco), and C6 peptide and scopolamine-injected group (C6+Sco), and were subjected to water maze training. Escape latency (second) of each water-maze learning day was recorded. The data were analyzed with two-way ANOVA, followed by a post hoc Newman-Keuls multiple-comparison tests. Data are represented as the mean±SEM. In comparison with the control group, *, $p<0.05$; **, $p<0.01$.

Both C5 peptide and C6 peptide ameliorate scopolamine-induced spatial learning and memory deficits. The Example uses Sco-induced amnesia animal model to investigate the effects of C5 peptide and C6 peptide on aging and dementia. FIG. 7 shows the average escape latency (second) of each group of rats in each water-maze learning day. Rats receiving Sco injection showed longer escape latency in finding the hidden platform ($F_{3,20}=10.36$, $P<0.01$). A significant improvement in escape latency was observed from Day 3 in (C5+Sco) and (C6+Sco) treated groups ($q=6.58$ and $6.77$, both $P<0.01$) in a comparison of rats receiving Sco injection. Additionally, from Day 3, rats in (C5+Sco) and (C6+Sco) treated groups found the hidden platform faster than rats in negative control group. The results indicate that C5 peptide and C6 peptide ameliorate scopolamine-induced memory impairment in spatial learning.

Example 6

Effects of C5 Peptide and C6 Peptide on Scopolamine-Induced Memory Deficits—Inhibitory Avoidance Memory Test 1. Animals.

Rats were obtained and taken care of as described in Example 4.

2. Materials

C5 peptide and C6 peptide were prepared by the methods described in Example 1. Scopolamine hydrochloride (Sco) was prepared by the methods described in Example 5.

3. Drug Treatment

Rats were intraperitoneally injected with Sco, C5 peptide and Sco (C5+Sco group), C6 peptide and Sco (C6+Sco group), and DMSO/PBS (negative control group), respectively, as described in Example 5.

4. Inhibitory Avoidance Learning Task

The apparatus consisted of a trough-shaped alley divided by a sliding door that separates an illuminated safety compartment and a dark compartment. A shock generator that produced current was connected to the floor of the dark compartment (UGO Basile, Comerio VA, Italy). The behavioral task, including the training and testing procedures, was recorded between 8:00 AM and 6:00 PM. Before the experiment, the rats were habituated in a dim room for 1 hour so that they could adjust to the environment. In the training phase, a rat was placed at the far end of the illuminated compartment facing away from the door. As the rat turned around, the door shut, and a 1 mA/s footshock was given twice. The rat was then removed from the alley and returned to its cage. At different times after training (1 day and 7 days later), the retention test was given. Rats were tested after 1 day and 7 days in the same manner as in the training, but without receiving a shock. Testing was terminated either when the rat entered the dark chamber or after 600 seconds without entry. Rats that did not enter the dark compartment and reached the ceiling score of 600 seconds were removed from the alley and assigned as rats with good memory. The animals placed in the dark compartment who received footshock (1 mA/s for 2 seconds) directly were assigned to the footshock-only control group.

5. Statistical Analysis.

The data were analyzed with one-way ANOVA, followed by a post hoc Newman-Keuls multiple-comparison test.

6. Results

Figure 8:
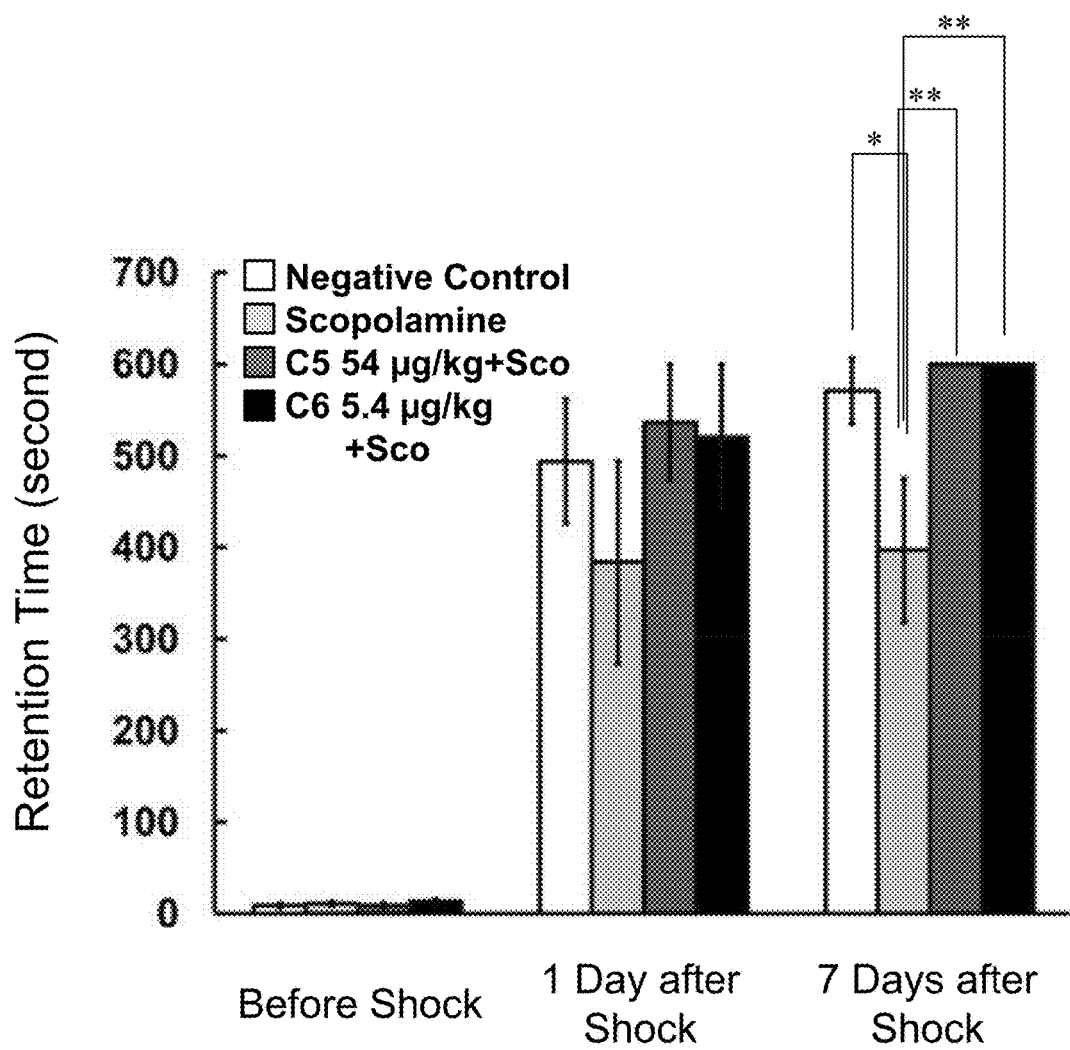
FIG. 8 shows effects of C5 peptide and C6 peptide on scopolamine-induced memory impairment in passive one-way inhibitory avoidance learning in rats. Rats were randomly divided into control, scopolamine-injected group (Sco), C5 peptide and scopolamine-injected group (C5+Sco), and C6 peptide and scopolamine-injected group (C6+Sco), and were subjected to passive one-way inhibitory avoidance learning. Retention time in an illuminated compartment before footshock did not show any difference. Retention time in an illuminated compartment 1 day and 7 days after footshock was recorded. The data were analyzed with one-way ANOVA, followed by a post hoc Newman-Keuls multiple-comparison tests. Data are represented as the mean±SEM. In comparison with the control group, *, $p<0.05$; **, $p<0.01$.

Both C5 peptide and C6 peptide ameliorate scopolamine-induced memory deficits. Rats were randomly divided into negative control group, scopolamine only group, (C5+Sco) group and (C6+Sco) group, and rats in the four groups were intraperitoneally injected with vehicle (negative control group and scopolamine only group), C5 peptide (54 µg/kg/day)(C5+Sco group), and C6 peptide (5.4 µg/kg/day)(C6+Sco group), respectively, for 14 consecutive days. After that, rats in the 4 groups were intraperitoneally injected with vehicle (negative control group), vehicle and scopolamine (1.5 mg/kg/day) (Scopolamine only group), C5 peptide (54 µg/kg/day) and scopolamine (1.5 mg/kg/day) (to C5+Sco group), and C6 peptide (5.4 µg/kg/day) and scopolamine (1.5 mg/kg/day) (C6+Sco group), respectively, for 7 consecutive days. Then, behavioral experiments were conducted, and the injection program with scopolamine continued through the experimentation. The injection volume was 1 µL/g of body weight. The scopolamine injection was performed 30 minutes before behavioral experiments every morning, and the C5 peptide or C6 peptide injection was conducted once daily at 5:00 PM 1 day prior. As shown in FIG. 8, before receiving the footshock, all the rat groups spent approximately the same time entering the dark chamber from an illuminated chamber ($P>0.05$). Sco-treated rats showed less retention time in the illuminated chamber 7 days after the footshock ($q=4.14$, $P<0.05$) (in a comparison of the control vs Sco-treated group on Day 7). (C5+Sco)-treated rats showed longer retention time in the illuminated chamber 7 days after the footshock ($q=4.84$, $P<0.05$) (in a comparison of the Sco vs (C5+Sco)-treated group on Day 7). So does (C6+Sco)-treated rats ($q=4.84$, $P<0.05$) (in a comparison of the Sco vs (C6+Sco)-treated group on Day 7). The results indicate that C5 peptide and C6 peptide ameliorate scopolamine-induced memory impairment in passive one-way avoidance tasks.

Example 7

Effects of C5 Peptide and C6 Peptide on Scopolamine-Induced Memory Deficits—Step-Down Passive Avoidance Test 1. Animals.

Rats were obtained and taken care of as described in Example 4.

2. Materials

C5 peptide and C6 peptide were prepared by the methods described in Example 1. Scopolamine hydrochloride (Sco) was prepared by the methods described in Example 5.

3. Drug Treatment

Rats were intraperitoneally injected with Sco, C5 peptide and Sco (C5+Sco group), C6 peptide and Sco (C6+Sco group), and DMSO/PBS (negative control group), respectively, as described in Example 6.

4. Step-Down Passive Avoidance Test

Animals were familiar to the instrument 24 hours before training. Next day rats placed on the elevated platform situated in the center of the floor of the passive avoidance test box and the latency to stepping down recorded. On the third day of the experiment immediately after stepping down, animals received mild electric shock (3V, 3 seconds duration, D.C.) through the grid floor and then returned to their home cages. On the following day (as 24 hours retention interval) rats placed on the platform again while no electric shock was given to them. Latency to step down recorded. If the rat remained on the platform for the 5 minutes, it assigned a maximum score of 300 seconds.

5. Statistical Analysis.

The data were analyzed with one-way ANOVA, followed by a post hoc Newman-Keuls multiple-comparison test.

6. Results

Figure 9A:
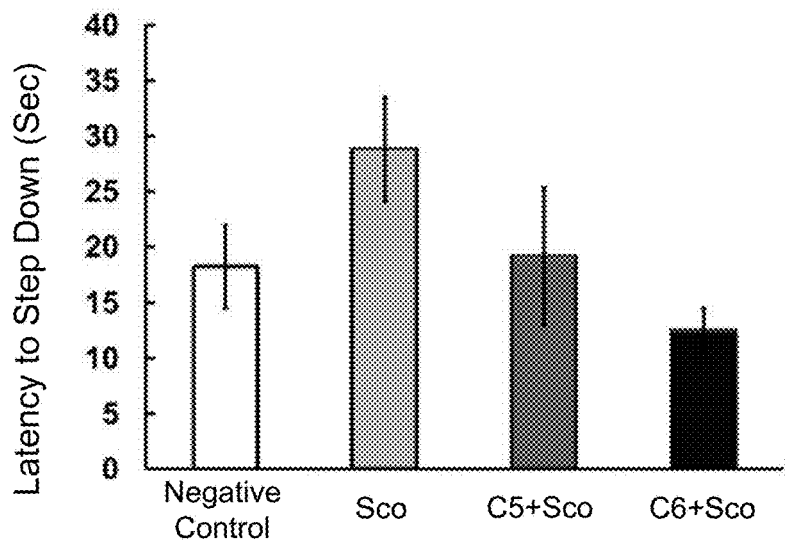
FIGS. 9A to 9C show effects of C5 peptide and C6 peptide on scopolamine-induced memory impairment in step-down passive avoidance memory task in rats. Rats were randomly divided into control, scopolamine-injected group (Sco), C5 peptide and scopolamine-injected group (C5+Sco), and C6 peptide and scopolamine-injected group (C6+Sco), and were subjected to step-down passive avoidance memory task.
Figure 9B:
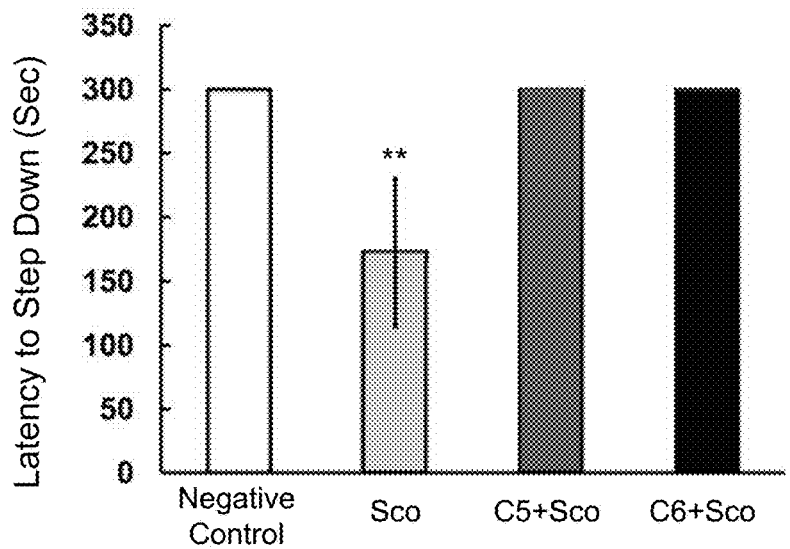
Figure 9C:
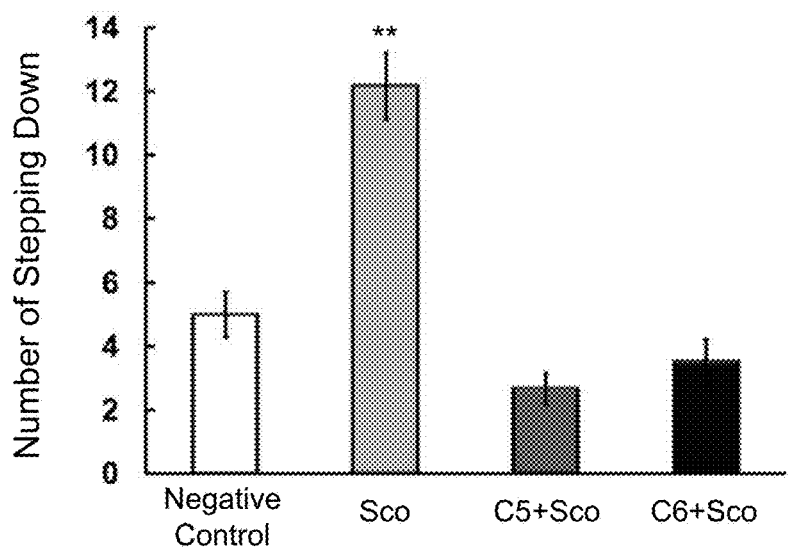

Both C5 peptide and C6 peptide ameliorate scopolamine-induced memory deficits. Rats were randomly divided into negative control group, Scopolamine only group, (C5+Sco) group and (C6+Sco) group, and rats in the four groups were injected with vehicle (negative control group and scopolamine only group), C5 peptide (54 µg/kg/day, C5+Sco group), and C6 peptide (5.4 µg/kg/day, C6+Sco group), respectively, for 14 consecutive days. After that, rats in the 4 groups were intraperitoneally injected with vehicle (negative control group), vehicle and scopolamine (1.5 mg/kg/day)(scopolamine only group), C5 peptide (54 µg/kg/day) and scopolamine (1.5 mg/kg/day) (C5+Sco group), and C6 peptide (5.4 µg/kg/day) and scopolamine (1.5 mg/kg/day) (C6+Sco group), respectively, for 7 consecutive days. Then, behavioral experiments were conducted, and the injection program with scopolamine continued through the experimentation. The injection volume was 1 µL/g of body weight. The scopolamine injection was performed 30 minutes before behavioral experiments every morning, and the C5 peptide or C6 peptide injection was conducted once daily at 5:00 PM 1 day prior. As shown in FIG. 9A, before receiving the footshock, all the rat groups spent approximately the same time jumping down the stage (P>0.05). As shown in FIG. 9B and FIG. 9C, after footshock, Sco-treated rats showed less retention time on the stage and stepped down more on 1 day after the footshock (q=4.4, P<0.05) (in a comparison of the control vs Sco-treated group on Day 1). (C5+Sco)-treated rats showed longer retention time on the stage and stepped down less on 1 day after the footshock (q=4.4, P<0.05) (in a comparison of the Sco vs (C5+Sco)-treated group on Day 1). (C6+Sco)-treated rats showed longer retention time on the stage and stepped down less on 1 day after the footshock (q=4.4, P<0.05) (in a comparison of the Sco vs (C6+Sco)-treated group on Day 7). The results indicate that C5 peptide and C6 peptide ameliorate scopolamine-induced memory impairment in step-down passive avoidance tasks.

Example 8

Effects of C5 Peptide and C6 Peptide on Scopolamine-Induced Memory Deficits in Object Recognition—Novel Object Recognition Learning Test 1. Animals.

Rats were obtained and taken care of as described in Example 4.

2. Materials

C5 peptide and C6 peptide were prepared by the methods described in Example 1. Scopolamine hydrochloride (Sco) was prepared by the methods described in Example 5.

3. Drug Treatment

Rats were intraperitoneally injected with Sco, C5 peptide and Sco (C5+Sco group), C6 peptide and Sco (C6+Sco group), and DMSO/PBS (negative control group), respectively, as described in Example 5.

4. Novel Object Recognition Learning

During familiarization, rats were allowed to explore 2 identical objects in an open field box (90×70×60 cm) for 5 min. The criteria used for exploration were a distance less than 1.5 cm between the rat and the object or direct contact with the object. During the retention test given 3 hours and 24 hours later, the rats were returned to the same box, but one of the familiar objects was replaced with a novel object of approximately the same size. The time that each rat spent exploring the 2 objects during a 5-min period was recorded. The rats placed in the open field box without any objects for 5 min were assigned to the non-trained group.

5. Statistical Analysis.

The data were analyzed with two-way ANOVA, followed by a post hoc Newman-Keuls multiple-comparison tests.

6. Results

Figure 10:
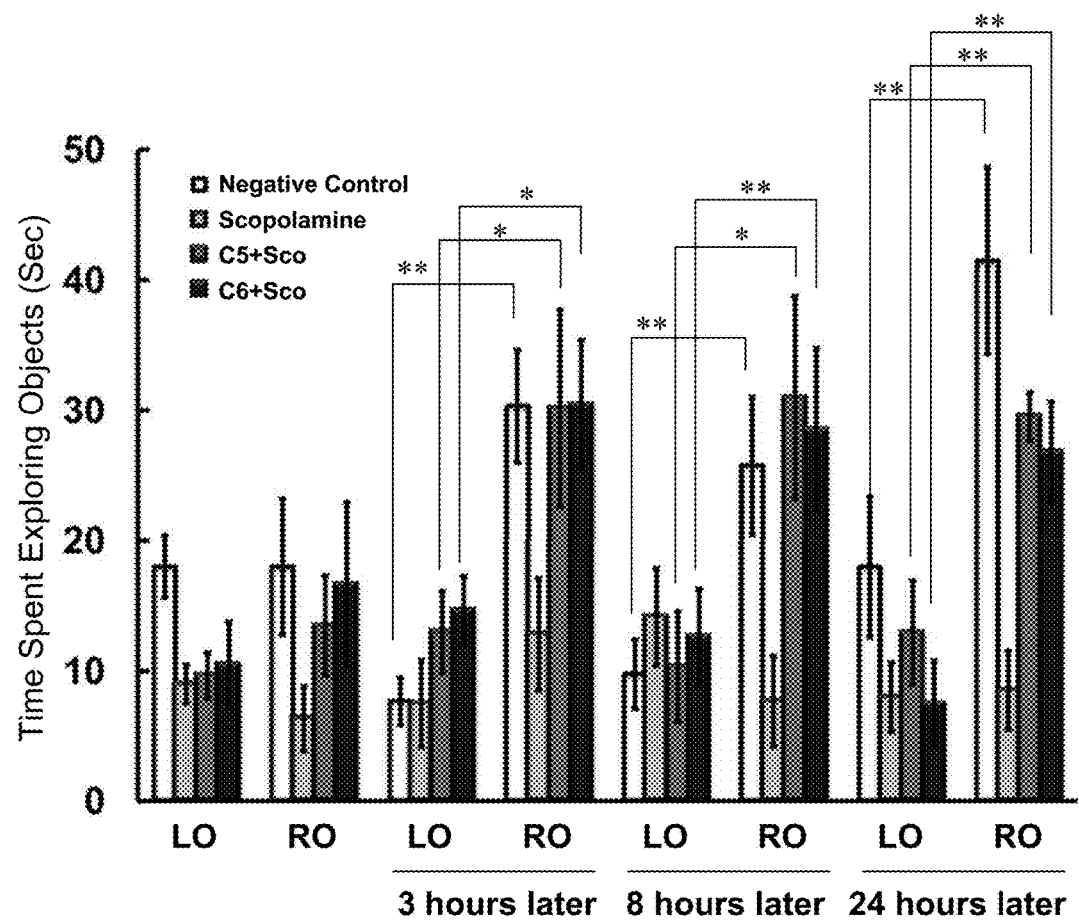
FIG. 10 shows effects of C5 peptide and C6 peptide on scopolamine-induced memory impairment in novel object recognition test in rats. Rats were randomly divided into control, scopolamine-injected group (Sco), C5 peptide and scopolamine-injected group (C5+Sco), and C6 peptide and scopolamine-injected group (C6+Sco), and were subjected to the novel object recognition test. The retention time (second) spent on exploring the left object (LO), right object (RO), and novel object (NO) before and 3 hours, 8 hours, and 24 hours after the right object was replaced with the novel object was recorded. The data were analyzed with two-way ANOVA, followed by a post hoc Newman-Keuls multiple-comparison tests. Data are represented as the mean±SEM. In comparison with the control group, *, $p<0.05$; **, $p<0.01$.

Both C5 peptide and C6 peptide ameliorate scopolamine-induced memory deficits. In the novel object recognition task, rats were randomly divided into negative control group, Scopolamine only group, (C5+Sco) group and (C6+Sco) group, and rats in the four groups were injected with vehicle (negative control group and scopolamine only group), C5 peptide (54 µg/kg/day, C5+Sco group), and C6 peptide (5.4 µg/kg/day, C6+Sco group), respectively, for 14 consecutive days. After that, rats in the 4 groups were intraperitoneally injected with vehicle (negative control group), vehicle and scopolamine (1.5 mg/kg/day)(scopolamine only group), C5 peptide (54 µg/kg/day) and scopolamine (1.5 mg/kg/day) (C5+Sco group), and C6 peptide (5.4 µg/kg/day) and scopolamine (1.5 mg/kg/day) (C6+Sco group), respectively, for 7 consecutive days. Then, behavioral experiments were conducted, and the injection program with scopolamine continued through the experimentation. The injection volume was 1 µL/g of body weight. The scopolamine injection was performed 30 minutes before behavioral experiments every morning, and the C5 peptide or C6 peptide injection was conducted once daily at 5:00 PM 1 day prior. As shown in FIG. 10, the animals did not show any preference for the left object (LO) or the right object (RO) during recognition training (all P>0.05). Three (3) hours, 8 hours and 24 hours after, a novel object (NO) replaced the RO. Control, (C5+Sco) and (C6+Sco)-treated rats showed a preference for the NO (q=3.87, P<0.05; q=3.57, P<0.05). Rats receiving Sco injection showed no exploratory preference for the NO with respect to time spent on exploring the LO (P>0.05) (each N=6). The results indicate that C5 peptide and C6 peptide ameliorate scopolamine-induced memory impairment in novel object recognition learning test.

Example 9

Effects of C5 Peptide and C6 Peptide on Spatial Learning and Memory in Aged Rats—Water Maze Task 1. Animals.

Rats were obtained and taken care of as described in Example 4.

2. Materials

C5 peptide and C6 peptide were prepared by the methods described in Example 1.

3. Drug Treatment

Before drug administration, 12-month-old rats were randomly divided into 4 groups and subjected to water maze training. Rats were then injected with PBS (negative control), C5 peptide (54 µg/kg/day), and C6 peptide (5.4 µg/kg/day), respectively, for 6 months prior to the behavioral test and persistently injected during the experimentation (N=6 for each group). The injection volume was 1 µL/g of body weight. The injections were performed once per day.

4. Water Maze Learning

Method of water maze learning is described in Example 4.

5. Statistical Analysis.

The data were analyzed with two-way ANOVA, followed by a post hoc Newman-Keuls multiple-comparison tests.

6. Results

Figure 11A:
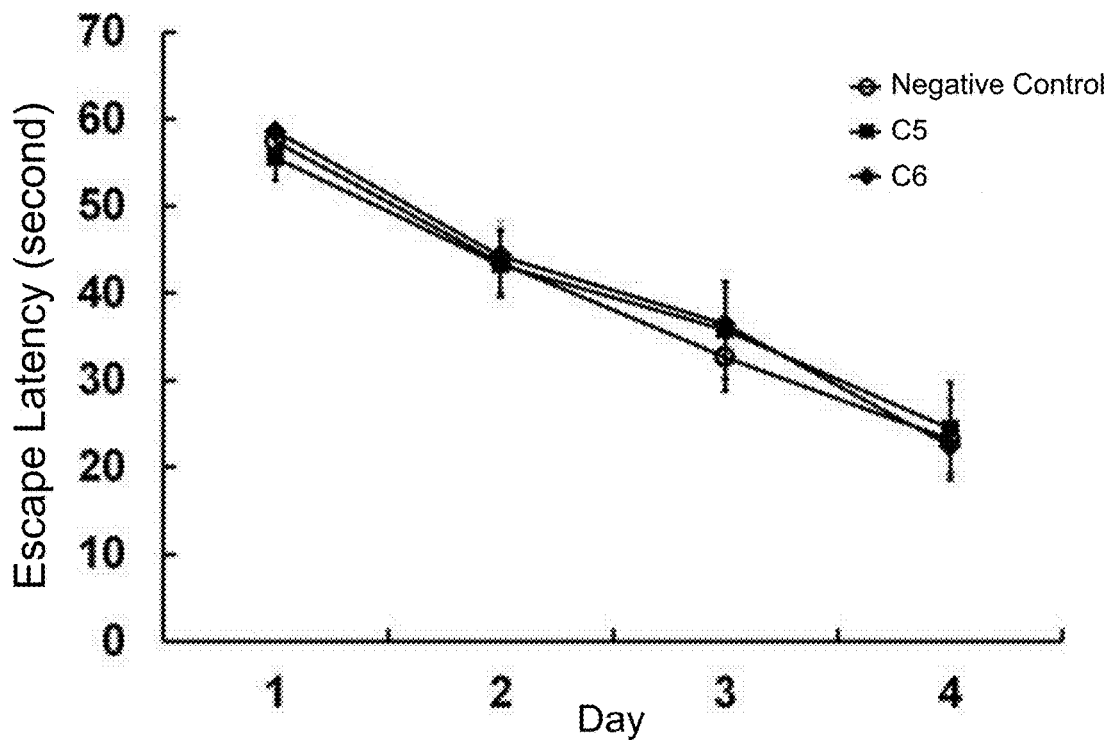
FIGS. 11A and 11B show effects of C5 peptide and C6 peptide on aging-induced memory impairment in water maze memory formation in rats. Aged rats were randomly divided into control, C5 peptide-injected group, and C6 peptide-injected group, and were subjected to water maze training.
Figure 11B:
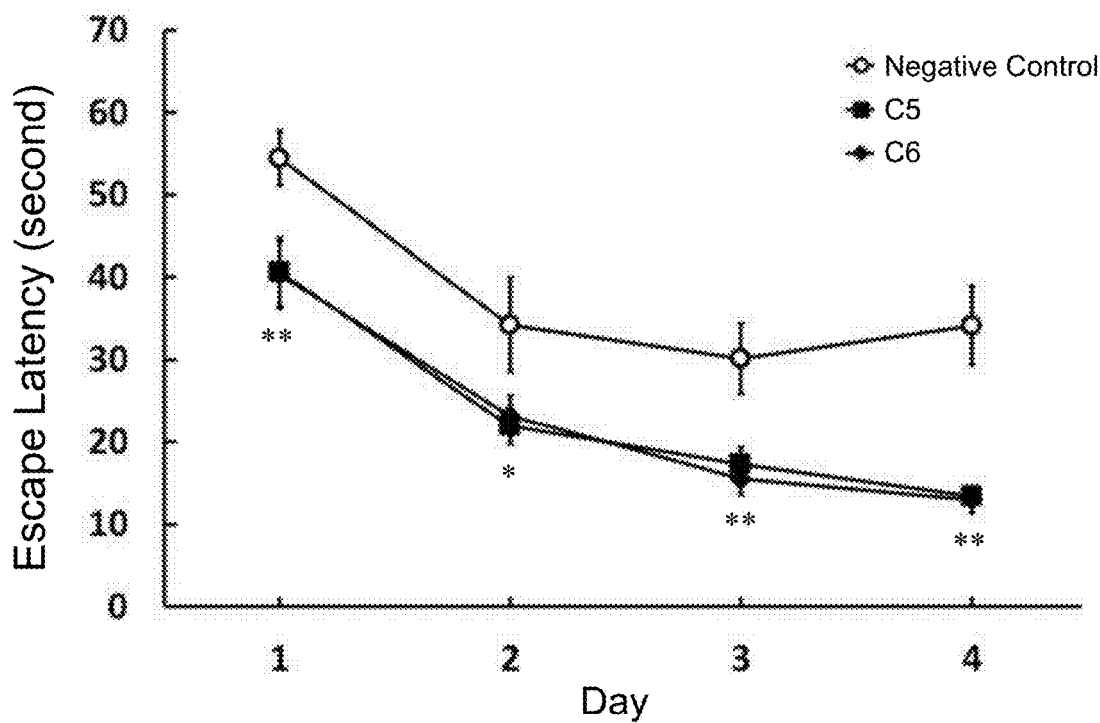

Both C5 peptide and C6 peptide ameliorate aging-induced memory deficits. Before drug administration, 12-month-old rats were randomly divided into 4 groups and subjected to water maze training. The training results are shown in FIG. 11A, in which the average escape latency (second) of each group was similar and decreased over the 4-day training period. After 6 months of drug administration, the 18-month-old rats were subjected to water maze test, and the results are shown in FIG. 11B. Compared to the rats of the negative control, rats receiving C5 peptide (54 µg/kg) or C6 peptide (5.4 µg/kg) injection showed shorter escape latency in finding the hidden platform, and a marked improvement in escape latency was observed from Day 1 in C5 and C6 treated groups ($p<0.01$). The results indicate that C5 peptide and C6 peptide ameliorate aging-induced memory impairment in spatial learning.

Figure 12:
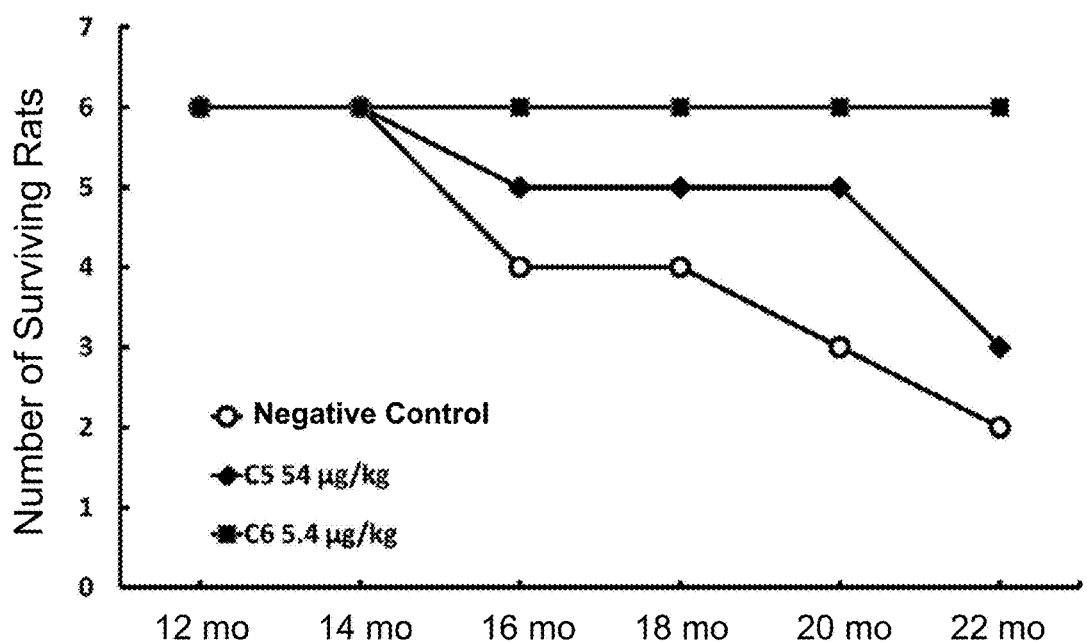
FIG. 12 shows effect of C5 peptide and C6 peptide on survival surveillance of aged rats. Each group (control, C5, and C6 groups) had 6 rats (12 months old) at the beginning of this test. Rat number in each group were recorded at the beginning of this test and every other month (12, 14, 16, 18, 20, and 22 months old, respectively). Data show the numbers of survival surveillance in each group.

In addition, survival surveillance of each group were recorded at the beginning of this test and every other month (12, 14, 16, 18, 20, and 22 months old, respectively). FIG. 12 shows the survival surveillance of the aged rats. Compared to the rats of the negative control, rats receiving C5 peptide injection had higher survival rates, and rats receiving C6 peptide injection had 100% survival surveillance at the age of 22 months. The results indicate that C5 peptide and C6 peptide prolong life expectancy of rats.

Example 10

Effects of C6 Peptide on 1-Methyl-4-Phenyl-1,2,3,6-Tetrahydropyridine (MPTP)-Mouse Model of Parkinson's Disease 1. Animals.

Rats were obtained and taken care of as described in Example 4.

2. Materials

C6 peptide was prepared by the methods described in Example 1. 1-methyl-4-phenyl-1,2,3,6-tetrahydropyridine (MPTP) was purchased from Sigma-Aldrich Co. (St. Louis, Mo., USA) and dissolved in DMSO for further use.

3. Drug Treatment

C57BL/6 male mice at the age of 5 weeks were randomly divided into 3 groups and intraperitoneally injected with PBS (negative control), MPTP (30 mg/kg)(MPTP group), and C6 peptide (10.7 µg/kg) and MPTP (30 mg/kg)(C6+MPTP group), respectively. The injection volume was calculated based on the body weight of each mouse everyday. Mice of the C6+MPTP group were injected C6 peptide for 3 weeks prior to injection of C6 peptide and MPTP for 1 week, and then subjected to rotarod performance test.

4. Rotarod Performance Test

Rotarod performance tests were conducted to measure the coordination of mice. Mice were placed on the rod and ran at 2 rpm constant speed for 2 minutes in order to adapt to the rod. After that, rod was started to accelerate to 20 rpm (within 5 minutes) and sustained for 15 minutes. The time (latency) at which each mouse fell off the rod was recorded.

5. Statistical Analysis.

The data were analyzed with one-way ANOVA, followed by a post hoc Newman-Keuls multiple-comparison tests.

6. Results

Figure 13:
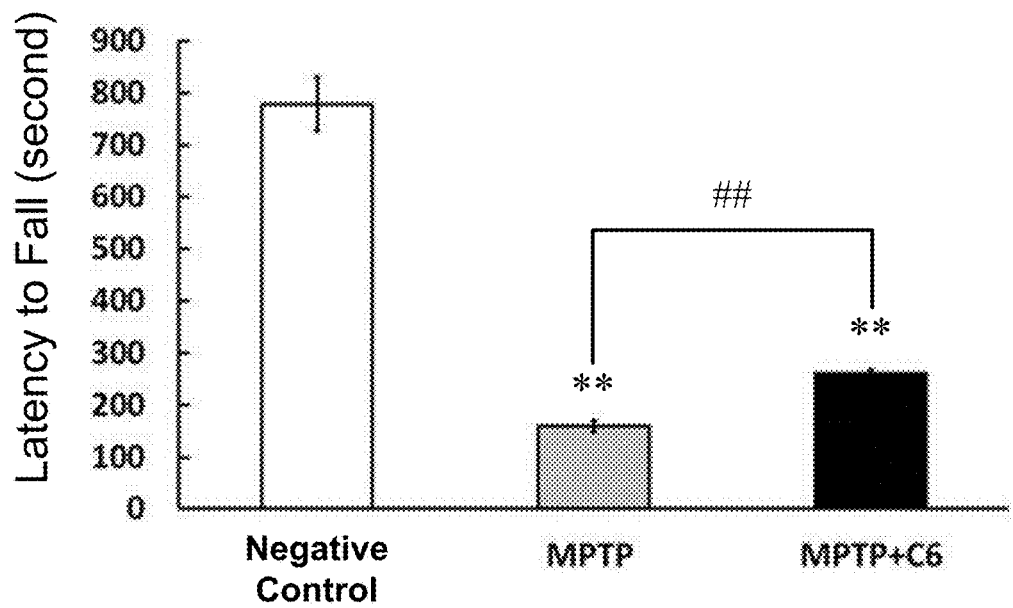
FIG. 13 shows effects of C6 peptide on 1-methyl-4-phenyl-1,2,3,6-tetrahydropyridine (MPTP)-mouse model of Parkinson's disease.

C6 peptide improves coordination in the MPTP-mouse model of Parkinson's disease. In this embodiment, MPTP was used to induce Parkinson's disease in mice, and the mouse model was used to study the effect of C6 peptide on Parkinson's disease. FIG. 13 shows the average latency to fall (second) of each group of mice on the rod. The longer the mice stayed on the rod, the better their coordination is. The average latency to fall of the mice injected PBS (negative control) was 778.5 seconds, the average latency to fall of the MPTP-mouse model of Parkinson's disease (MPTP group) was 159.8 seconds, and the average latency to fall of the (MPTP+C6) group was 261 seconds. A significant decrease in latency to fall was observed in both the MPTP group and the (MPTP+C6) group in a comparison of the negative control ($q=24.12$, 23.42, 20.18, $p<0.01$). Mice in the (MPTP+C6) group showed significantly longer latency to fall than the MPTP-mouse model of Parkinson's disease (MPTP group) did ($q=4.19$, 3.45, $p<0.05$). The results indicate that C6 peptide improves coordination in the MPTP-mouse model of Parkinson's disease.

Example 11

Effects of C5 Peptide and C6 Peptide on Spatial Learning and Memory in D-Galactose Induced Aging Model Rats—Water Maze Task 1. Animals.

Rats were obtained and taken care of as described in Example 4.

2. Materials

C5 peptide and C6 peptide were prepared by the methods described in Example 1. D-galactose was purchased from Sigma-Aldrich Co. (St. Louis, Mo., USA) and dissolved in 0.9% NaCl solution for further use.

3. Drug Treatment

Sprague-Dawley rats at the age of 7 weeks were randomly divided into negative control group (0.9% NaCl), D-galactose-injected group (D-galactose), C5 peptide and D-galactose-injected group (C5+D-galactose), and C6 peptide and D-galactose-injected group (C6+D-galactose). Rats in the 4 groups were intraperitoneally injected with 0.9% NaCl (negative control group and D-galactose group), C5 peptide (54 µg/kg/day, C5+D-galactose group), and C6 peptide (5.4 µg/kg/day, C6+D-galactose group), respectively, for 7 consecutive days. After that, rats in the 4 groups were intraperitoneally injected with 0.9% NaCl (negative control group), 0.9% NaCl and D-galactose (150 mg/kg/day)(D-galactose group), C5 peptide (54 µg/kg/day) and D-galactose (150 mg/kg/day) (C5+D-galactose group), and C6 peptide (5.4 µg/kg/day) and D-galactose (150 mg/kg/day) (C6+D-galactose group), respectively, for 9 consecutive weeks, and then were subjected to water maze tasks. The injection volume was 1 µL/g of body weight.

4. Water Maze Learning

Method of water maze learning is described in Example 4.

5. Statistical Analysis.

The data were analyzed with two-way ANOVA, followed by a post hoc Newman-Keuls multiple-comparison tests.

6. Results

Figure 14:
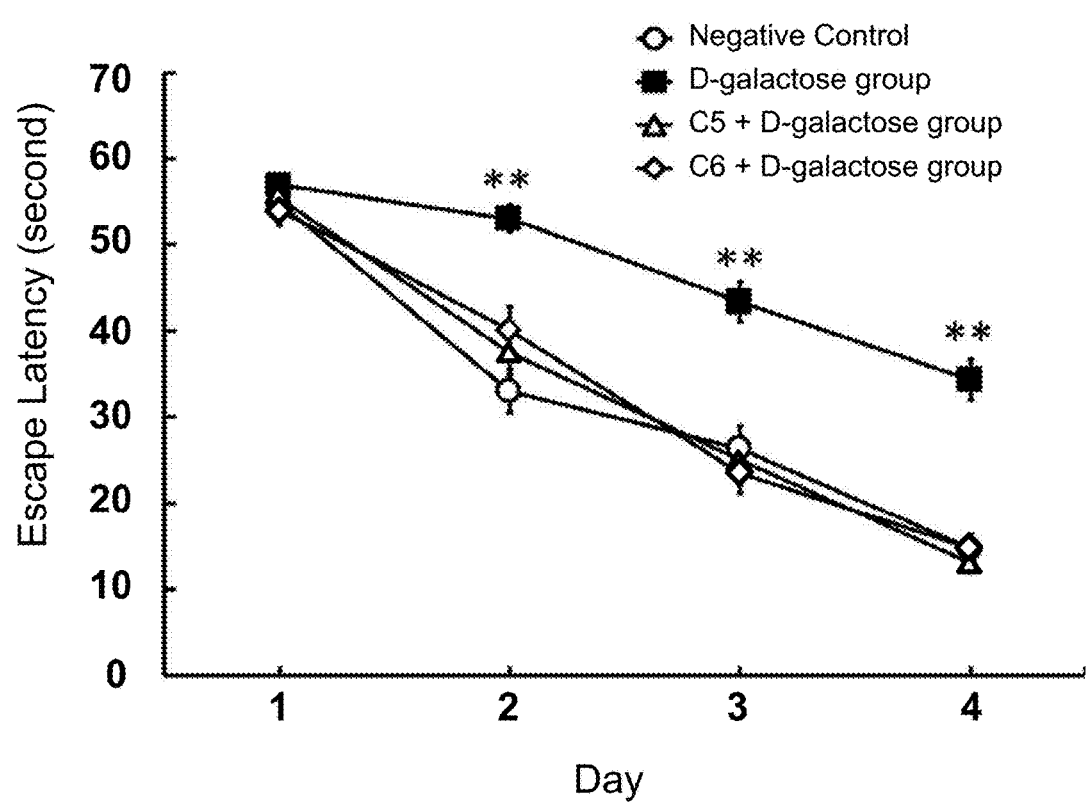
FIG. 14 shows effect of C5 peptide and C6 peptide on D-galactose induced aging in water maze memory formation in rats. Rats were randomly divided into control, D-galactose-injected group, C5 peptide and D-galactose-injected group, and C6 peptide and D-galactose-injected group, and were subjected to water maze training. Escape latency (second) of each water-maze learning day was recorded. The data were analyzed with two-way ANOVA, followed by a post hoc Newman-Keuls multiple-comparison tests. Data are represented as the mean±SEM. In comparison with the control group, **, $p<0.01$.

Both C5 peptide and C6 peptide enhance spatial learning and memory in D-Galactose induced aging model rats. FIG. 14 shows the average escape latency (second) of each group of rats in each water-maze learning day. Rats receiving D-Galactose injection showed longer escape latency in finding the hidden platform (average latency was 53.06 seconds). A significant improvement in escape latency was observed from Day 2 in C5+D-Galactose and C6+D-Galactose groups (q=5.34, 4.3'7, p<0.01) in a comparison of rats receiving D-Galactose injection, but no significant difference was observed among negative control, C5+D-Galactose, and C6+D-Galactose groups (p>0.05). The results indicate that C5 peptide and C6 peptide enhance spatial learning and memory in D-Galactose induced aging model rats.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A peptide enhancing neuronal outgrowth, consisting of the following sequence:

Asn-$X_1$-$X_2$-Pro-Gln          (SEQ ID NO: 3), wherein $X_1$ is an amino acid selected from the group consisting of nonpolar amino acids; and $X_2$ is an amino acid selected from the group consisting of naturally occurring amino acids and amino acid analogs;

wherein the peptide enhances neuronal outgrowth.

2. The peptide of claim 1, wherein the sequence is selected from the group consisting of NAIPQ (SEQ ID NO: 1), NPSPQ (SEQ ID NO: 2), NFEPQ (SEQ ID NO: 4), NMYPQ (SEQ ID NO: 5), NIKPQ (SEQ ID NO: 6), NLMPQ (SEQ ID NO: 7), NVAPQ (SEQ ID NO: 8), and NWLPQ (SEQ ID NO: 9).

3. A composition, comprising a peptide of claim 1 and a pharmaceutically acceptable vehicle.

4. A method for enhancing neuronal outgrowth, comprising contacting a neuronal cell with a peptide of claim 1 in an amount sufficient to enhance neuronal outgrowth.

5. The method of claim 4, wherein the neuronal cell is normal or damaged.

* * * * *

SEQUENCE LISTING

```
<160> NUMBER OF SEQ ID NOS: 9

<210> SEQ ID NO 1
<211> LENGTH: 5
<212> TYPE: PRT
<213> ORGANISM: Artificial Sequence
<220> FEATURE:
<223> OTHER INFORMATION: Peptide for enhancing neuronal outgrowth

<400> SEQUENCE: 1

Asn Ala Ile Pro Gln
1               5

<210> SEQ ID NO 2
<211> LENGTH: 5
<212> TYPE: PRT
<213> ORGANISM: Artificial Sequence
<220> FEATURE:
<223> OTHER INFORMATION: Peptide for enhancing neuronal outgrowth

<400> SEQUENCE: 2

Asn Pro Ser Pro Gln
1               5

<210> SEQ ID NO 3
<211> LENGTH: 85
<212> TYPE: PRT
<213> ORGANISM: Artificial Sequence
<220> FEATURE:
<223> OTHER INFORMATION: Peptide for enhancing neuronal outgrowth
<220> FEATURE:
<221> NAME/KEY: MOD_RES
<222> LOCATION: (1)..(40)
<223> OTHER INFORMATION: Xaa = any amino acid, Xaa at positions 1-40 may
      be present or absent
<220> FEATURE:
<221> NAME/KEY: MOD_RES
<222> LOCATION: (42)..(42)
<223> OTHER INFORMATION: Xaa = any nonpolar amino acid
```

-continued

```
<220> FEATURE:
<221> NAME/KEY: MOD_RES
<222> LOCATION: (43)..(43)
<223> OTHER INFORMATION: Xaa = any amino acid
<220> FEATURE:
<221> NAME/KEY: MOD_RES
<222> LOCATION: (46)..(85)
<223> OTHER INFORMATION: Xaa = any amino acid, Xaa at positions 46-85
      may be present or absent

<400> SEQUENCE: 3

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Asn Xaa Xaa Pro Gln Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa
            85

<210> SEQ ID NO 4
<211> LENGTH: 5
<212> TYPE: PRT
<213> ORGANISM: Artificial Sequence
<220> FEATURE:
<223> OTHER INFORMATION: Petide for enhancing neuronal outgrowth

<400> SEQUENCE: 4

Asn Phe Glu Pro Gln
1               5

<210> SEQ ID NO 5
<211> LENGTH: 5
<212> TYPE: PRT
<213> ORGANISM: Artificial Sequence
<220> FEATURE:
<223> OTHER INFORMATION: Petide for enhancing neuronal outgrowth

<400> SEQUENCE: 5

Asn Met Tyr Pro Gln
1               5

<210> SEQ ID NO 6
<211> LENGTH: 5
<212> TYPE: PRT
<213> ORGANISM: Artificial Sequence
<220> FEATURE:
<223> OTHER INFORMATION: Petide for enhancing neuronal outgrowth

<400> SEQUENCE: 6

Asn Ile Lys Pro Gln
1               5

<210> SEQ ID NO 7
<211> LENGTH: 5
<212> TYPE: PRT
<213> ORGANISM: Artificial Sequence
<220> FEATURE:
<223> OTHER INFORMATION: Petide for enhancing neuronal outgrowth

<400> SEQUENCE: 7
```

```
Asn Leu Met Pro Gln
1               5

<210> SEQ ID NO 8
<211> LENGTH: 5
<212> TYPE: PRT
<213> ORGANISM: Artificial Sequence
<220> FEATURE:
<223> OTHER INFORMATION: Petide for enhancing neuronal outgrowth

<400> SEQUENCE: 8

Asn Val Ala Pro Gln
1               5

<210> SEQ ID NO 9
<211> LENGTH: 5
<212> TYPE: PRT
<213> ORGANISM: Artificial Sequence
<220> FEATURE:
<223> OTHER INFORMATION: Petide for enhancing neuronal outgrowth

<400> SEQUENCE: 9

Asn Trp Leu Pro Gln
1               5
```